(12) United States Patent
Lukac et al.

(10) Patent No.: US 9,572,632 B2
(45) Date of Patent: Feb. 21, 2017

(54) LASER SYSTEM AND METHOD FOR OPERATING THE LASER SYSTEM

(71) Applicant: Fotona d.d., Ljubljana (SI)

(72) Inventors: Matjaz Lukac, Ljubljana (SI); Marko Kazic, Dob (SI)

(73) Assignee: Fotona d.o.o, Ljubljana (SI)

( * ) Notice: Subject to any disclaimer, the term of this patent is extended or adjusted under 35 U.S.C. 154(b) by 96 days.

(21) Appl. No.: 14/621,413

(22) Filed: Feb. 13, 2015

(65) Prior Publication Data

US 2015/0223911 A1    Aug. 13, 2015

(30) Foreign Application Priority Data

Feb. 13, 2014   (EP) ..................................... 14000529

(51) Int. Cl.
| A61C 15/00 | (2006.01) |
| A61C 1/00 | (2006.01) |
| A61C 17/02 | (2006.01) |
| A61B 18/20 | (2006.01) |
| A61N 5/06 | (2006.01) |
| A61N 5/067 | (2006.01) |
| A61B 18/26 | (2006.01) |

(52) U.S. Cl.
CPC ........... *A61C 1/0069* (2013.01); *A61B 18/201* (2013.01); *A61C 1/0046* (2013.01); *A61C 17/0202* (2013.01); *A61N 5/0603* (2013.01); *A61N 5/0624* (2013.01); *A61B 2018/263* (2013.01); *A61N 5/062* (2013.01); *A61N 2005/067* (2013.01); *A61N 2005/0644* (2013.01)

(58) Field of Classification Search
CPC ...... A61C 5/02; A61C 1/0069; A61C 17/0202
See application file for complete search history.

(56) References Cited

U.S. PATENT DOCUMENTS

| 6,234,765 | B1 * | 5/2001 | Deak ......................... F04F 7/00 417/321 |
| 6,538,739 | B1 | 3/2003 | Visuri et al. |
| 7,980,854 | B2 | 7/2011 | Glover et al. |
| 2006/0111697 | A1 | 5/2006 | Brinkmann et al. |
| 2010/0021983 | A1 | 1/2010 | Vogel |
| 2014/0342303 | A1 * | 11/2014 | Altshuler ........... A61C 17/0202 433/29 |
| 2015/0010882 | A1 * | 1/2015 | Bergheim .............. A61C 17/02 433/80 |

* cited by examiner

*Primary Examiner* — Robert N Wieland
(74) *Attorney, Agent, or Firm* — Gudrun E. Huckett

(57) ABSTRACT

A dental irrigation system is provided with a laser source for generating a laser beam and an optical delivery system for the laser beam. The laser beam wavelength ranges from 0.4 µm to 11.0 µm. The laser system operates in pulsed operation with pulse sets of 2 to 20 individual pulses of temporally limited pulse length. The pulse sets follow one another with temporal separation. The individual pulses follow one another with pulse repetition rate. The laser system generates at least one vapor bubble within the liquid irradiated with the laser beam. A single pulse causes the vapor bubble to oscillate between a maximal and a minimal volume with a bubble oscillation frequency. The pulse repetition rate within one pulse set is adjusted relative to the bubble oscillation frequency such that synchronization between delivery of the pulses and bubble oscillation is achieved.

47 Claims, 8 Drawing Sheets

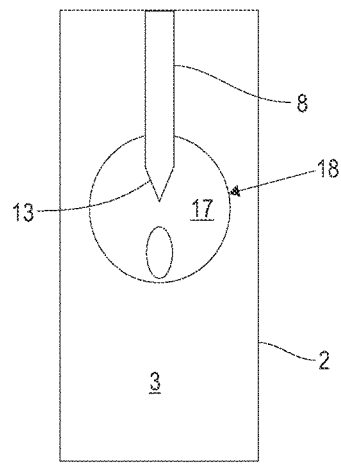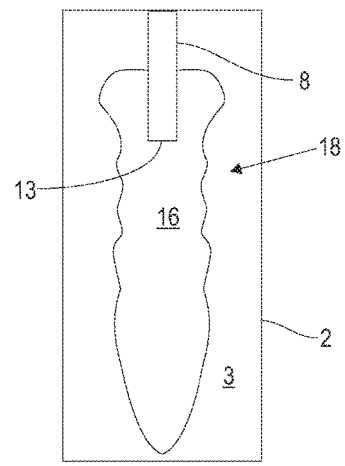
*Fig. 5a*  *Fig. 5b*
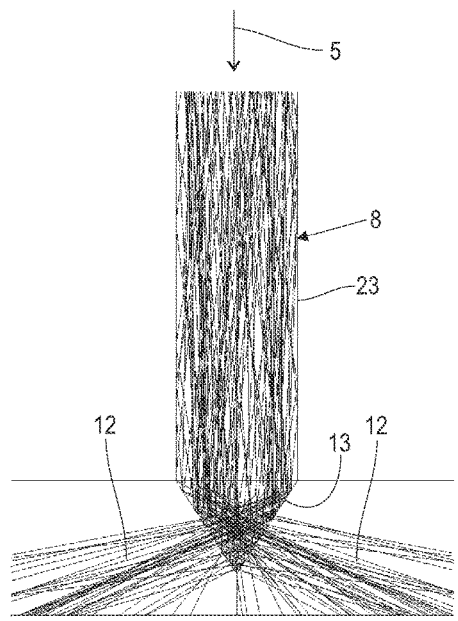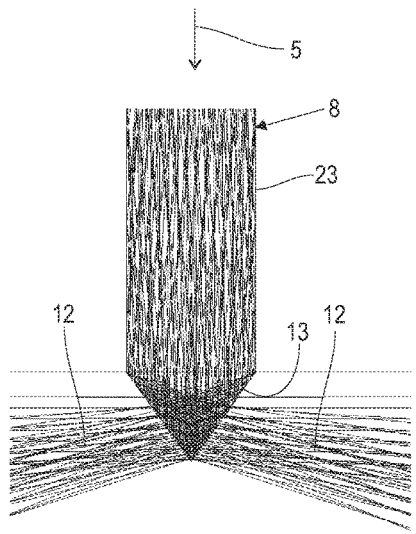
*Fig. 6a*  *Fig. 6b*

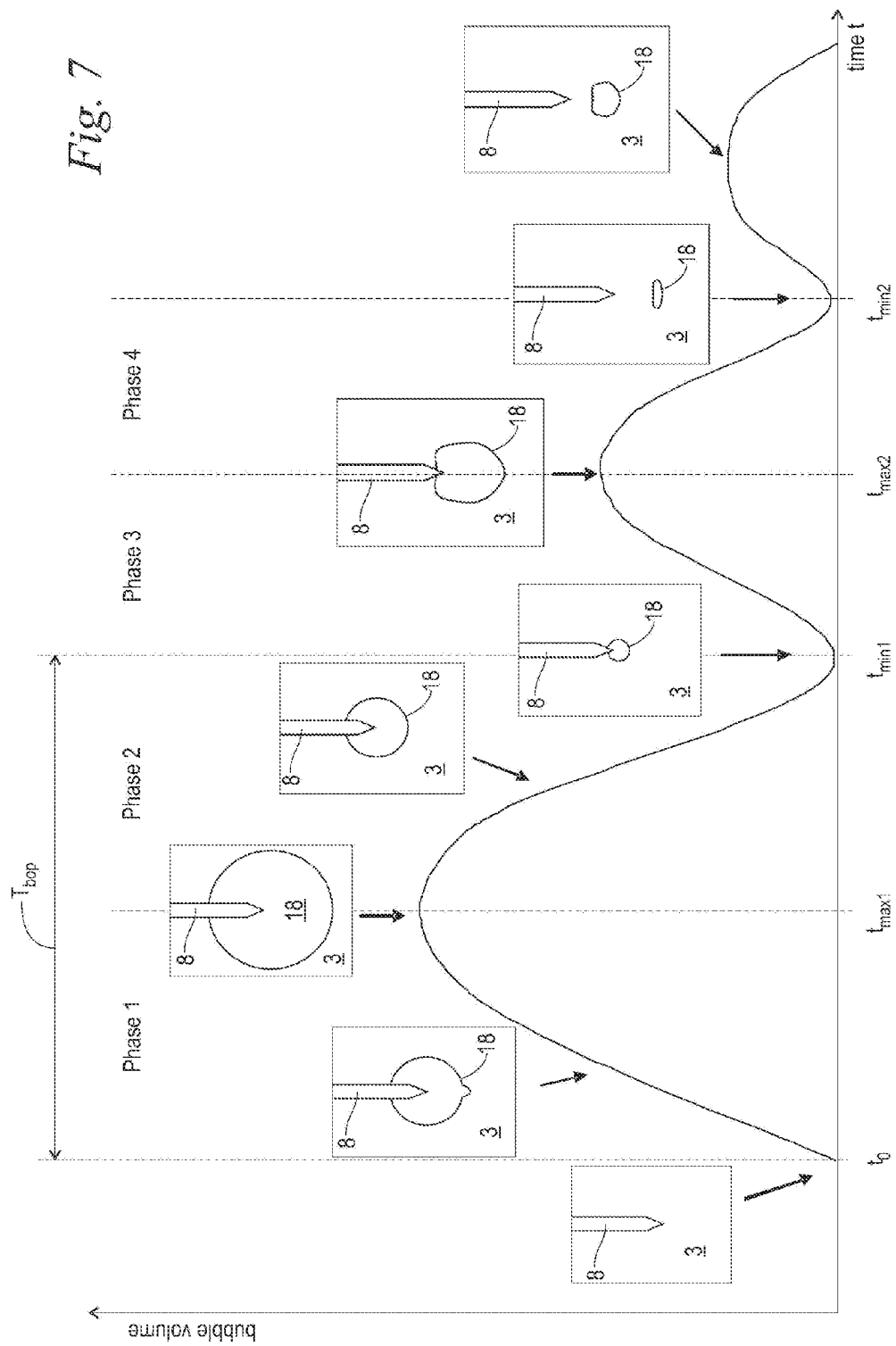

LASER SYSTEM AND METHOD FOR OPERATING THE LASER SYSTEM

BACKGROUND OF THE INVENTION

The present invention relates to a laser system for irrigation, including debriding, cleaning and decontamination, of anatomical cavities filled with a liquid.

There are many medical treatments, such as in endodontics, periodontics, implantology, or bone surgery where an effective irrigation, including debriding, cleaning and decontamination of the anatomical cavities is desirable.

For example, a goal of endodontic treatment is typically to obtain an effective cleaning and decontamination of the root canal system (e.g., removal of bacteria and other contaminants from the smear layer). Clinically, traditional endodontic techniques use mechanical instruments as well as ultrasound and chemical irrigation, in an attempt to shape, clean and completely decontaminate the endodontic system.

The complexity of the root canal system is well known. Numerous lateral canals (with various dimensions and with multiple morphologies) branch off from the principal canals. The effectiveness of debriding, cleaning and decontaminating effectively all the intra-radicular space is often limited, given the anatomical complexity and given the inability of common irrigants to penetrate into the lateral canals and/or the apical ramifications. A debriding, cleaning and decontaminating effectively of the root system thus represents a challenge.

Similarly, when creating a hole in hard body tissue like bone material, using the mechanical tools such as drill or saw, tissue particles debris is left on the tissue surface leading to a smear layer on the treated surface. This may lead to increased inflammatory response and decelerated tissue regeneration and attachment. This is for example important in implantology where faster attachment of the bone to the inserted implants is crucial for faster patient recovery time. A minimally invasive improved means for the cleaning, debriding and disinfection of the holes created during bone surgery are therefore desirable. Also, in order to stop inflammations that occur after the surgery, and to promote re-attachment, an improved means for the cleaning, debriding and disinfection of the surfaces of the already inserted implants and the surrounding bone surfaces are also desirable.

Use of lasers has been studied in endodontics since the early 1970s, and lasers are now widely used in dental applications. Early attempts at laser use in endodontics typically resulted in occlusion of dentinal tubules, thereby undesirably decreasing their permeability. Some early reports indicated a reduction of bacterial load, although in connection with unwanted generation of heat. More recent investigations have focused on laser-activated irrigation approaches that produce explosive vapor bubbles with acoustic transients effects, facilitating removal of debris from intricate tooth anatomy. These approaches permit fluid interchange and the removal of organic tissue and microbes, resulting in tubular dentin disinfection.

In a prior laser irrigation method (for example, as disclosed in U.S. Pat. No. 7,980,854), a laser system contains a source of a laser light beam. An elongate optical fiber is connected to the laser source and is configured to transmit the laser light beam to a tip. The tip is substantially completely immersed into a liquid introduced into the open area of a pulp chamber to provide a liquid reservoir. In this prior laser irrigation method, the laser source is pulsed at a power level from about 0.1 watts to about 1.5 watts, at a pulse duration from about 100 nanoseconds to about 1000 microseconds, at a pulse frequency from about 2 Hertz (Hz) to about 25 Hz, and over a cycle time of from about 10 seconds to about 40 seconds. In this prior system, solid state lasers having a wavelength of from about 700 nanometers (nm) to about 3000 nm are contemplated, such as Nd:YAG (neodymium-doped yttrium aluminum garnet), Er:YAG (erbium-doped yttrium aluminum garnet), Ho:YAG (holmium-doped yttrium aluminum garnet), Nd:YLF (neodymium-doped yttrium lithium fluoride), titanium sapphire, or Er,Cr:YSSG (erbium, chromium doped yttrium scandium gallium garnet) lasers. The interaction of the pulsed laser beam with the liquid is contemplated to result in a rinsing, irrigating and disinfecting of the pulp chamber and root canal to provide substantially clean and pulp-free dentin walls lining the chamber and root canal ready for subsequent filling.

In this prior method, laser pulses are delivered into the liquid at a relatively slow repetition rate of 2 to 25 Hz. There is therefore no substantial interaction between the acoustic transients caused by individual pulses, resulting in a limited laser light-to-acoustic (LA) energy conversion efficiency. Even more importantly, in this prior art method, the bacteria within the treated anatomical cavity are submitted to acoustic transients of a relatively short duration. It is well known, however, that when bacteria are submitted to increased temperatures, the kill rate depends not only on the amplitude of the temperature increase, but even more importantly, on the temporal duration of the temperature increase, the exact dependence being described by the standard Arrhenius integral. Similar consideration applies also when bacteria are submitted to acoustic transients. When subjected to acoustic transients, the bacteria's structure is disrupted and the bacteria die, providing that the exposure to the transients is extensive enough to be fatal. Bacteria kill rate will be much higher when bacteria are submitted to acoustic transients for a longer duration of time, preferably longer than 1000 μs. Accordingly, even after disclosure of prior laser irrigation methods, it remains desirable to provide improved laser irrigation devices and/or methods wherein the laser treatment parameters are adjusted and/or optimized to obtain stronger and longer lasting acoustic transients.

Moreover, the prior art method requires that the laser energy is delivered into the liquid reservoir within the pulp chamber and root canal in a "contact" manner, by means of an elongate optical fiber configured to transmit laser light beam from a laser source to a conical fiber tip which is substantially immersed into the liquid reservoir, and the light beam is emitted from the tip generally omnidirectionally. There are at least two shortcomings of this approach: i) Special tip is required to perform the treatment, which adds to the complexity and cost of the treatment. Moreover, the fiber tip is susceptible to damage since it can get at least partially shattered under the strong acoustic transients within the liquid. Undesirable fragmented fiber particles may therefore remain within the cavity after the treatment. This makes the prior art method less safe, and also less effective since the strength of the acoustic transients must be adjusted to be below the damage threshold of the fiber tip; ii) The angular distribution of a laser beam coming out of an elongate fiber is broad and omnidirectional with a lack of collimation, which results in insufficient laser energy conversion.

Accordingly, improved methods, techniques and technologies that can improve irrigation, including cleaning, debriding and disinfection of anatomical cavities (e.g., root canal systems, periodontal pockets, surgical holes and the like) are desirable. In particular, even after disclosure of prior laser irrigation methods, it remains desirable to provide improved, less invasive laser irrigation devices and/or methods wherein the laser treatment parameters are adjusted and/or optimized to obtain stronger and longer lasting acoustic transients without the need to increase the single pulse energy or the cumulative energy delivered to a liquid during a treatment.

The object of the present invention is to provide an improved laser system with a better laser energy conversion for improved irrigation results.

SUMMARY OF THE INVENTION

This object is solved by a dental irrigation system being configured for irrigation, including debriding, cleaning and decontamination, of open tooth cavities filled with a liquid, the irrigation system comprising a laser system and the liquid, wherein the laser system comprises a laser source for generating a laser beam and an optical delivery system for the laser beam, wherein the delivery system includes a treatment handpiece and an exit component, wherein the treatment handpiece and the exit component are configured to irradiate the liquid within the open tooth cavity with the laser beam, wherein a wavelength of the laser beam is in a range from above 0.4 µm to 11.0 µm inclusive, wherein the laser system is adapted to be operated in pulsed operation with pulse sets containing at least two and maximally twenty individual pulses (p) of a temporally limited pulse length ($t_p$), wherein the pulse sets follow one another with a temporal separation ($T_s$), and wherein the individual pulses (p) follow one another with a pulse repetition rate ($f_p$), wherein the laser system is adapted to generate at least one vapor bubble within the liquid when irradiated with the laser beam, wherein one single pulse (p) causes the at least one vapor bubble to oscillate between a maximal and a minimal volume with a bubble oscillation frequency ($f_b$), and wherein the pulse repetition rate ($f_p$) of the individual pulses (p) within one pulse set is adjusted relative to the bubble oscillation frequency ($f_b$) such, that a synchronization between the delivery of the pulses (p) and the bubble oscillation is achieved.

The present invention utilizes an improved scientific understanding of the interaction of pulsed laser light with a highly absorbing liquid. Namely, when a pulsed laser beam which is highly absorbed in liquids is delivered to such a liquid, a bubble oscillation sequence develops with a very high oscillation frequency in the range from about 1 kHz to about 10 kHz. By delivering laser energy to a liquid in temporally limited pulse sets containing up to twenty individual laser pulses, and adjusting the pulse repetition rate of the pulses to match the bubble oscillation dynamics, firstly an improved light-to-acoustic energy conversion is obtained, and secondly an extended duration of acoustic transients for better disinfection can be achieved. Moreover, according to a preferred embodiment of the invention, laser pulses may be delivered and synchronized with the bubble oscillation dynamics in such a manner that elongate bubbles with a channel like shape are formed, extending the length of the vapor bubble deeper into the liquid along the direction of the laser beam. Bubbles extending deeper into the liquid filled cavity are desirable, for example, when treating deep cavities. Additionally, when laser energy with a strongly absorbed wavelength is delivered to a liquid in a non-contact manner, creating extended, channel shaped bubbles is advantageous since it moves at least partially the bubble's energy away from the liquid surface, effectively reducing the undesirable influence of the liquid surface on the LA efficiency. However, it also can be expedient to form bubbles with a generally spherical shape, if the conditions require.

For the purposes of describing present invention, the conditions under which a laser light is highly absorbed in a liquid is roughly divided into a linear, or thermal regime, and a non-linear regime. A linear absorption regime applies when laser pulse power density in a liquid is not high enough to result in the ionization or in other non-linear interactions with water molecules. Typically, lasers with pulse durations in a microsecond or millisecond range (from one microsecond to about 5000 µs), such as flash-lamp pumped free-generation Er:YAG lasers, operate in a linear regime. In this regime, the intensity, or amplitude A, of a laser light exponentially diminishes with distance x within a liquid according to A exp (–kx), where k (in cm$^{-1}$) is a linear absorption coefficient of the liquid at the particular laser wavelength. The absorption coefficient k and the corresponding penetration depth, p=1/k, are strongly wavelength dependent. For example, the penetration depth of the Er:YAG laser wavelength of 2.94 µm in water is approximately 10$^{-4}$ cm while the penetration depth of the Nd:YAG laser wavelength of 1.064 mm is 1 cm. As will be shown below, "highly absorbed" wavelengths, defined here as wavelengths with a penetration depth p≤1000 µm in the linear regime, are more suitable for performing laser irrigation. According to this definition, laser wavelengths with p>1000 µm in the linear regime are defined as "weakly absorbed" wavelengths. For water, and other OH-containing liquids, the applicable range of highly absorbed wavelengths extends from about 1.3 µm, inclusive, to about 11 µm, and the applicable range of weakly absorbed wavelengths extends from about 0.4 µm to 1.3 µm.

At extremely high laser power densities, on the order of about of 10$^{10}$-10$^{11}$ W/cm$^2$, an "optical breakdown" as a result of the ionization of liquid molecules may occur, leading to an abrupt increase in liquid's absorption. In this, non-linear regime, a high absorption of laser light is observed even for weakly absorbed wavelengths, i.e., for wavelengths which have a long penetration depth p in the linear regime. Non-linear conditions are typically achieved with high pulse power Q-switched laser beams, with pulse durations, $t_p$ in a nanosecond range (from one nanosecond to about 85 ns), especially when these beams are focused into a sufficiently small volume of the liquid. It is to be appreciated that when an optical path of a weakly absorbed nanosecond beam has a focal point located within a liquid, the beam will propagate within the liquid without being appreciably absorbed until it reaches the focal region where the laser power density becomes sufficiently high for non-linear effects to occur. It is only at this point that a bubble formation will occur.

When a pulsed laser beam which is highly absorbed in liquids, either in a linear or non-linear regime, is delivered to such a liquid a bubble generation occurs. For laser pulse durations longer than approximately 1 nanosecond there are no shock waves created in the liquid during the bubble expansion. Instead, the energy stored in the bubble is converted into acoustic energy only after the bubble reaches its maximum size, and the difference in pressures forces the bubble to collapse. As a result, the bubble's energy ($E_B$) which can be used up for debriding, cleaning and disinfection of the anatomical cavities is proportional to the volume of the bubble at its maximal size ($V_{max}$). The bubble's energy, $E_B$ can be mathematically calculated from $$E_B = p \times V_{max} \tag{Eq. 1}$$

where p equals the hydrostatic pressure of the liquid, and equals $10^5$ Pa for water. The light-to-acoustic energy (LA) efficiency of the conversion of the laser pulse energy ($E_L$) into the energy of acoustic transients can therefore be written as $$\eta = E_B/E_L = p \times V_{max}/E_L \quad \text{(Eq. 2)}$$

Our studies have shown that for laser wavelengths with the penetration depth less than about 10 μm, the bubble's energy is proportional to the square of laser energy, and to the $1.5^{th}$ power of the pulse duration, according to $$E_B \sim E_L^2/t_p^{3/2} \quad \text{(Eq. 3)}$$

An obvious means for increasing the strength of acoustic transients is to increase the bubble's volume by increasing the laser pulse energy. However, increasing the acoustic transients by increasing the laser pulse energy has two important limitations. First limitation is given by dimensions of the anatomical cavity. Namely, for the efficient conversion of the bubble energy into acoustic transients it is advantageous that the bubble does not interact with the cavity walls. The bubble must therefore be preferentially smaller than the cavity dimensions. Assuming, for the purposes of explanation only, a maximum permissible spherical bubble diameter of 3 mm when performing a procedure in a root canal, this limits the largest permissible bubble volume to $V_B \leq 19$ mm$^3$. Experiments show that with an Er:YAG, 30 microseconds long laser pulse, delivered into water through a 400 μm thick optical conical fiber tip, a 3 mm bubble is generated by a laser pulse with approximately 15 mJ of energy. This means that under above conditions and assumptions, the Er:YAG laser pulse energy would be limited to a maximum of 15 mJ, and using Eq. 1, the energy of the generated acoustic transients following a single pulse would be limited to 1.5 mJ. A means for extending the temporal duration of transients, instead of substantially increasing their amplitude is therefore desirable. It is to be appreciated that when performing the aforementioned prior method, the temporal duration of the acoustic transients cannot be increased by increasing the laser pulse duration, since according to Eq. 3, the bubble's energy is smaller for longer pulse durations, and also the acoustic transients are typically emitted after the laser pulse has already ended, and the generated bubble is already in the collapse phase.

Second limitation is given by absorption characteristics of the treatment laser light in the liquid. Namely, the LA energy conversion efficiency is lower for lower absorption coefficients, being inversely proportional to the penetration depth. Our measurements revealed that under the same experimental conditions, the Nd:YAP (1.34 μm) laser, with an approximately 1000 times longer penetration depth in water than the Er:YAG (2.94 μm) laser, requires approximately 100 times higher laser pulse energy to produce the same size bubble. Assuming a linear absorption regime, Table 1 shows, for example, penetration depths in water for different laser wavelengths, and corresponding calculated laser pulse energies that are required to generate a 3 mm spherical bubble. Calculated LA efficiencies ($\eta$) are also shown. Calculations are based on the experimental observation described above that at the Er:YAG laser wavelength of 2.94 mm, with the optical penetration depth of approximately 1 μm in water, an energy of 15 mJ is required to generate a spherical bubble with a 3 mm diameter using a 400 μm conical fiber tip. Calculations are made only for the purposes of describing the invention. The values for the penetration depths are therefore only approximate. Note also that calculations were made under the assumption that for all wavelengths the laser pulse duration and fiber tip geometry were the same as with the measured Er:YAG laser. The exact values of the required laser energies and therefore of the LA conversion efficiencies will depend on the exact penetration depths, fiber tip diameters and shapes, pulse duration, bubble dimensions and shape, treated cavity dimensions and shape, liquid characteristics etc. It is also to be noted that absorption enhancing additives may be added to a liquid, thus significantly reducing the penetration depth of otherwise weekly absorbed wavelengths in the liquid.

TABLE 1

Dependence of LA energy conversion efficiency $\eta$, on laser wavelength.

| Laser type | Wavelength (in μm) | Penetration depth in water (in μm) | Laser pulse energy $E_L$ | $\eta$ |
|---|---|---|---|---|
| Er:YAG | 2.94 | 1 | 0.015 J | 13% |
| Ho:YAG | 2.1 | 100 | 0.15 J | 1.3% |
| Nd:YAP | 1.34 | 1,000 | 1.5 J | 0.13% |
| Nd:YAG | 1.064 | 10,000 | 15 J | 0.013% |
| Ti:saphire | 0.700 | 1,000,000 | 1.500 J | 0.00013% |

Low LA energy conversion efficiency is not desirable for several reasons. Firstly, more powerful laser devices are required to generate required pulse energies and repetition rates. Even more importantly, the amount of heat H, that remains deposited in a liquid following a laser pulse, depends on the required $E_L$ and $\eta$ as $H = E_L (1-\eta)$. The maximal cumulative (total) laser energy, represented by a sum of all single pulse energies delivered during a treatment, that may be delivered into a liquid during a treatment, without overheating it, can be calculated by taking into account the specific heat capacity of water of 4200 J/kgK. It is important to note that the temperature gets increased by more than about 5 degrees Celsius, an irreversible damage to the dental pulp will occur. Assuming now, for example, a volume of the treated root canal of 5 mm$^3$ the heat energy that would elevate the temperature of the water filled root canal by a safe temperature difference of 3.5 degrees Celsius, is equal to H=73.5 J. By turning now to Table 1, we can conclude that with the Nd:YAG laser wavelength, for example, where the required single pulse energy is 15 J, and $\eta=0.013\%$, this temperature increase will be reached following a delivery of only five consecutive Nd:YAG laser pulses. In order to avoid overheating of the treated anatomical cavities, it is thus desirable to increase the LA conversion efficiency, especially when wavelengths with longer penetration depths in the linear regime are being used.

In the aforementioned prior method, the single pulse energies of the laser are in the range from about 3 mJ to about 750 mJ, and the treatment wavelength range extends from 700 nm to 3000 nm. This is a very wide range, and depending on the treatment laser wavelength the treatment effects may be too small at lowest energies, while at higher energies the laser beam may not be substantially absorbed within the liquid and may, undesirably, interact directly with the root canal and/or the pulp, and/or increase the temperature of the liquid.

More generally, various shortcomings of prior medical devices and methods (for example, endodontic treatments) can be addressed by utilizing a medical and dental treatment system or other exemplary system configured in accordance with principles of the present disclosure. For example, a more efficacious disinfection of the treated anatomical cavities can be achieved. Additionally, laser ablation of the root canal may be reduced, minimized, and/or eliminated. Moreover, laser damage to tooth pulp may be reduced, minimized, and/or eliminated. Additionally, thermal damage arising from localized heating of a treatment liquid may be reduced, minimized, and/or eliminated. Also, a system configured in accordance with principles of the present disclosure requires lower output characteristics, and is therefore smaller and less costly to produce. Wavelengths (such as, for example, a Ho:YAG at 2.1 µm, or an Nd:YAP at 1.34 µm), otherwise less suitable for the treatment due to their lower absorption in liquid may be used as well. Moreover, in certain embodiments no fiber tip is required to be immersed into the liquid. Yet further, when utilized in connection with mechanical treatment of bone, residual smear layers of loose bone material may be cleared from the inner surface of a drilled hole.

For following the above mentioned inventive findings, the individual pulses as they are known in the prior art are in a preferred embodiment replaced by inventive pulse sets. The individual pulses are combined to pulse sets consisting of a minimum of two and maximally 20 individual pulses, with the intra-set pulse repetition rate synchronized with the vapor bubble oscillation dynamics in the frequency range from 1 kHz to 10 kHz, and the pulse sets being temporally separated from each other by at least 20 ms.

Improved understanding of the bubble formation has revealed that it is advantageous that the beam is emitted from the tip not omni-directionally but angularly focused generally in a radial direction with regard to the tip's longitudinal axis. This shortcoming of the prior art is in the present invention overcome by using in various embodiments an articulated arm instead of an elongate fiber to deliver the light beam from a laser source to the tip. Namely, due to different optical transmission properties of the two types of optical delivery, the angular distribution of a laser beam coming out of an elongate fiber is much broader and omni-directional than when coming out of an articulated arm where the beam remains approximately collimated.

The proposed laser system and method may be applied to any kind of an anatomical, or even industrial, cavity.

BRIEF DESCRIPTION OF THE DRAWINGS

Embodiments of the invention will be explained in the following with the aid of the drawing in more detail. With reference to the following description, appended claims, and accompanying drawings:

FIG. 5a illustrates an exemplary spherical vapor bubble generated by the application of a laser beam;

FIG. 5b illustrates an exemplary elongate vapor bubble generated by the application of a laser beam;

FIG. 6a illustrates the beam profile exiting a conical tip, when using an optical delivery component consisting of an elongate fiber.

FIG. 6b illustrates the beam profile exiting a conical tip, when using an optical delivery component consisting of an articulated arm.

FIG. 7 illustrates an exemplary vapor bubble oscillation sequence under influence of one short laser pulse;

DESCRIPTION OF PREFERRED EMBODIMENTS

Figure 1:
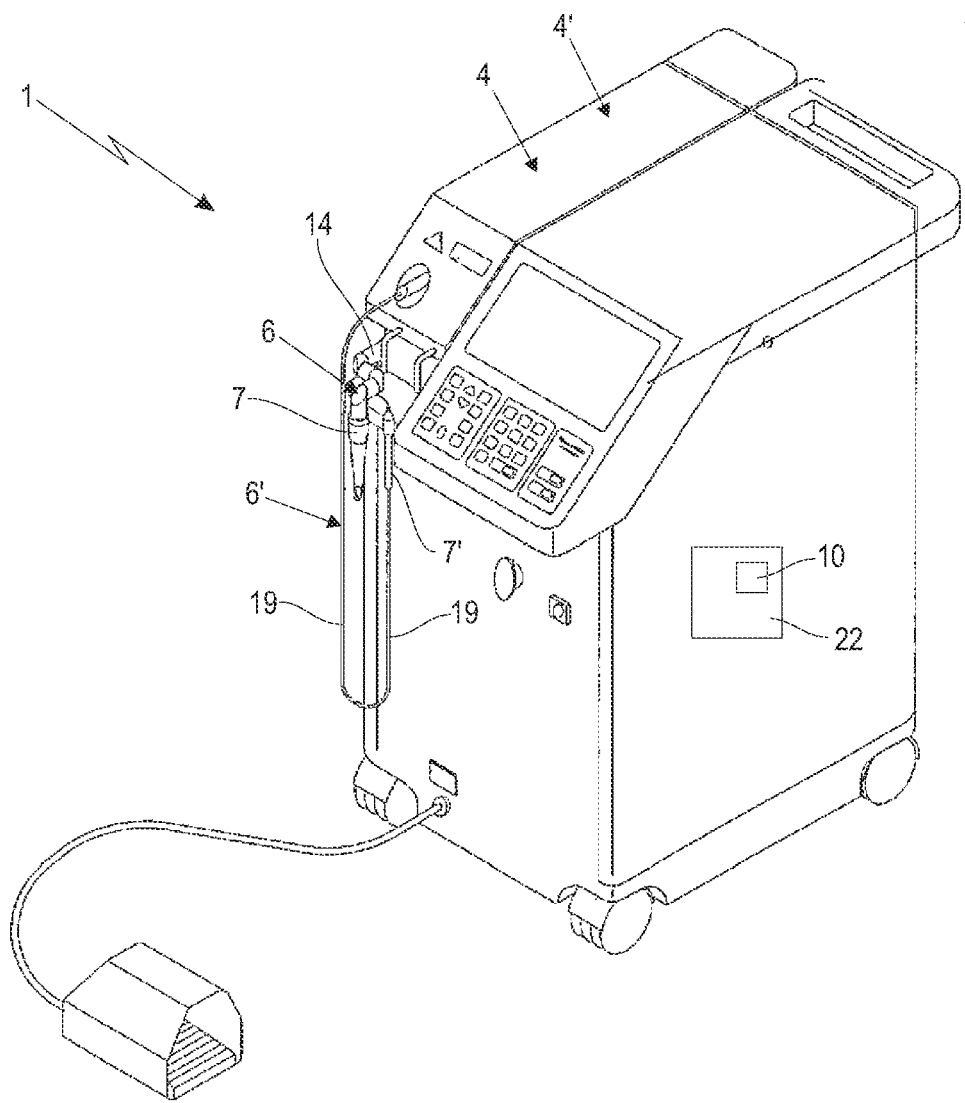
FIG. 1 illustrates an exemplary inventive laser system with both an optical fiber laser delivery system and an articulated arm laser delivery system.

With reference now to FIG. 1, in various embodiments, a medical treatment laser system 1 comprises at least one laser source 4 for generating a laser beam 5 (FIGS. 4a to 6b), and an optical delivery system 6 for the laser beam 5. The laser system further comprises a schematically indicated control unit 22 for controlling the laser beam 5 parameters, wherein the control unit 22 includes again schematically indicated adjusting means 10 for adjusting the laser beam 5 parameters as described below. The optical delivery system 6 preferably includes an articulated arm 14 and a treatment handpiece 7, wherein the laser beam 5 is transmitted, relayed, delivered, and/or guided from the laser source 4 through the articulated arm 14 and the handpiece 7 to a target. The articulated arm 14 might preferably be an OPTO-FLEX® brand articulated arm available from Fotona, d.d. (Slovenia). In the shown preferred embodiment a second laser source 4' and a second optical delivery system 6' with a second handpiece 7' is provided, wherein instead of the articulated arm a flexible elongated delivery fiber 19 for guiding the laser beam 5' is incorporated. Despite both laser sources 4, 4' and delivery systems 6, 6' being shown in combination, one of both in the alternative may be provided and used within the scope of the present invention. In this description, the expression medical laser systems is sometimes used, meaning both, medical and dental laser systems. Moreover, the medical treatment laser system 1 may be configured with any appropriate components and/or elements configured to facilitate controlled application of laser energy, for example, in order to create vapor bubbles in a liquid 3 within an anatomical cavity 2 for irrigation, including debriding, cleaning and decontamination of said anatomical cavity 2, as shown and described below.

It is to be understood that in order to perform laser irrigation according to the invention, the treated anatomical cavity 2 (FIGS. 2, 3) must be filled with a liquid 3. The cavity 2 may be filled spontaneously with blood or other bodily fluids by the body itself. Alternatively, the cavity may be filled with water, or other liquids such as disinfecting solutions, by the operator. Preferably, said liquid 3 is an OH-containing liquid, for example a liquid with its major portion being water.

Figure 9:
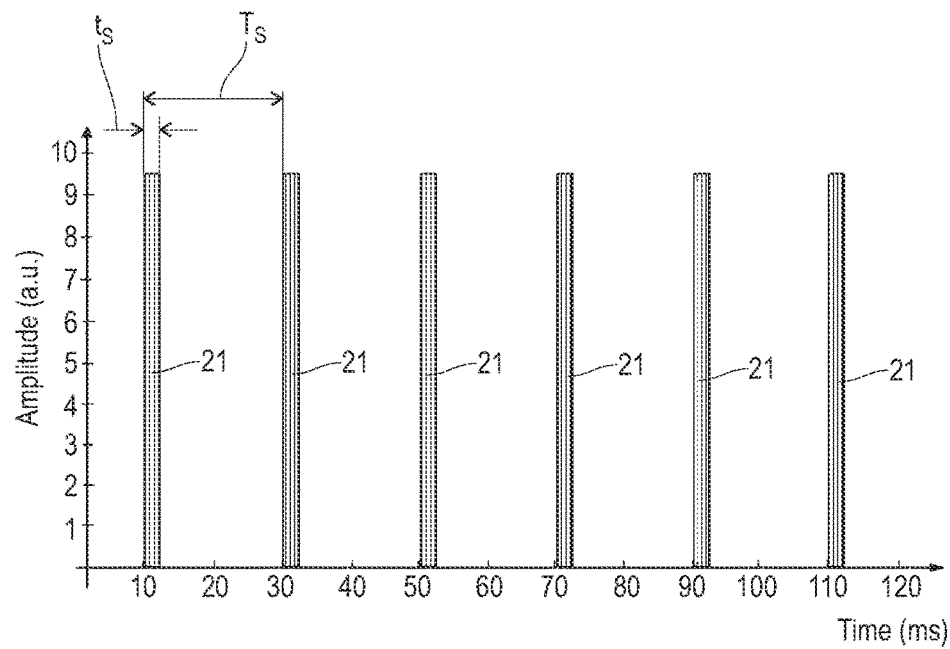
FIG. 9 represents a diagrammatic illustration of the temporal course of pulse sets in accordance with various embodiments of the invention.
Figure 10:
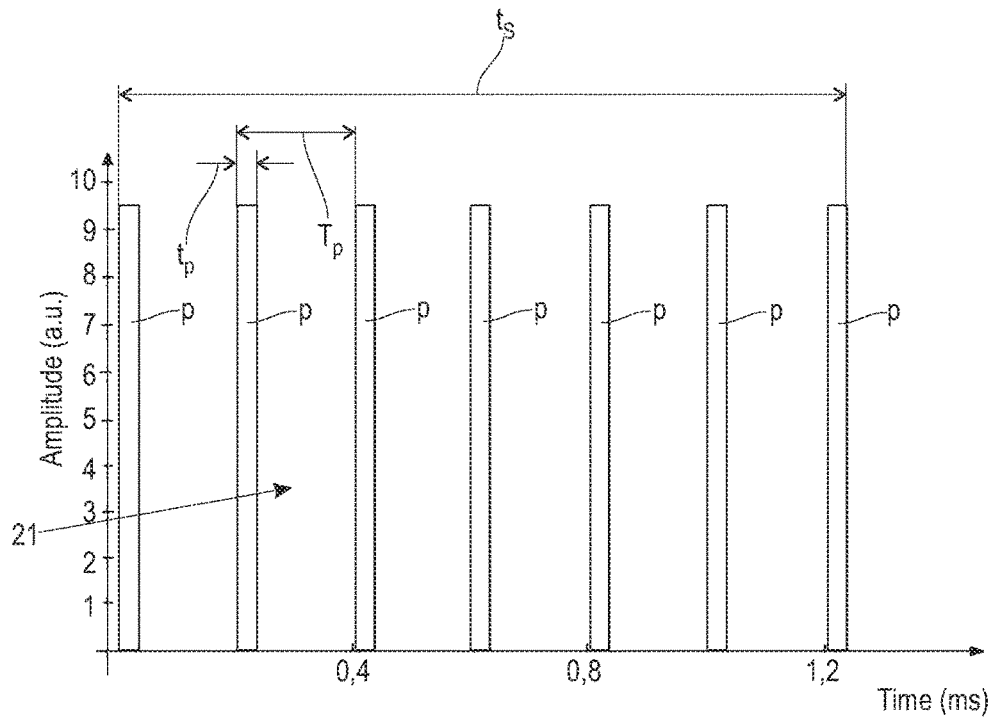
FIG. 10 represents and enlarged diagrammatic illustration of a detail of a pulse set according to FIG. 9 with the temporal course of individual pulses in accordance with various embodiments.

Either one of the laser sources 4, 4' is a pulsed laser. The laser source 4, 4' may be solid state, and configured with a pulse duration of less than 250 μs. The laser pulse duration is defined as the time between the onset of the laser pulse, and the time when 50% of the total pulse energy has been delivered to the liquid. The pulse duration may be fixed; alternatively, the pulse duration may be variable and/or adjustable. The pulse energy may be fixed; alternatively, the pulse energy may vary during the treatment. The wavelength of the laser beam 5 is in a range from above 0.4 μm to 11.0 μm inclusive. As illustrated in FIGS. 9, 10, the laser system 1 is adapted to be operated in pulsed operation with pulse sets containing at least two and maximally twenty individual pulses p of a temporally limited pulse length $t_p$, wherein a temporal separation $T_s$ between the pulse sets is ≥20 ms, and wherein the individual pulses p follow one another with a temporal pulse period $T_P$ within a range of 50 μs, inclusive, to 1000 μs, inclusive. The temporal pulse period reciprocal $1/T_P$ corresponds to a pulse repetition rate $f_p$. The pulse repetition rate $f_p$ is therefore preferably in a range from about 1 kHz to about 20 kHz.

The laser sources 4, 4', in particular the laser source 4 may desirably be configured to generate coherent laser light having a wavelength such that the laser beam 5 is highly absorbed in the liquid 3, wherein the laser pulse duration is in the range of ≥1 μs and <250 μs, and preferably of ≥1 μs and <120 μs. Preferably, the laser source 4, 4' is one of an Er:YAG laser source having a wavelength of 2940 nm, an Er:YSGG laser source having a wavelength of 2790 nm, an Er,Cr:YSGG laser source having a wavelength of 2780 nm or 2790 nm, or a $CO_2$ laser source having a wavelength of 9300 nm to 10600 nm, all of them providing a laser beam 5 highly absorbed in water and other OH-containing liquids. In the present preferred embodiment, the laser source 4 is an Er:YAG laser having a wavelength of 2940 nm, wherein the laser pulse energy is in a range from 1.0 mJ to 40.0 mJ, and preferably within a range from 5.0 mJ to 20.0 mJ. Alternatively, the laser sources 4, 4', in particular the laser source 4' may desirably be configured to generate coherent laser light having a wavelength such that the laser beam 5 is weakly absorbed in the liquid 3, wherein the laser pulse duration is in the range of ≥1 ns and <85 ns, and preferably of ≥1 ns and <25 ns. Preferably, the laser source 4, 4' is one of a Q-switched Nd:YAG laser source having a wavelength of 1064 nm, a Q-switched ruby laser source having a wavelength of 690 nm, or an alexandrite laser source having a wavelength of 755 nm, including laser sources 4, 4' with frequency doubled wavelengths of these laser sources 4, 4', all of them providing a laser beam 5 weakly absorbed in water and other OH-containing liquids. In the present preferred embodiment, the laser source 4' is the a.m. Q-switched Nd:YAG laser source.

Moreover, any other suitable laser source 4, 4' may be utilized, as desired. In certain embodiments, the laser source 4, 4' may be installed directly into the handpiece 7, 7', and no further laser light delivery system 6, 6' such as the articulated arm 14 or elongated delivery fiber 19 is required.

Figure 2A:
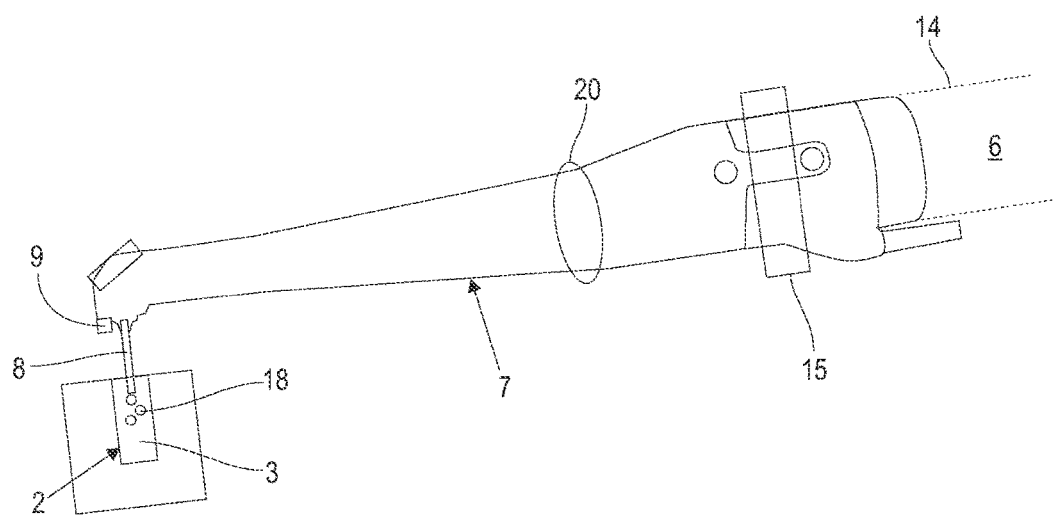
FIG. 2a illustrates an exemplary treatment handpiece fed by an articulated arm in contact operational mode.
Figure 2B:
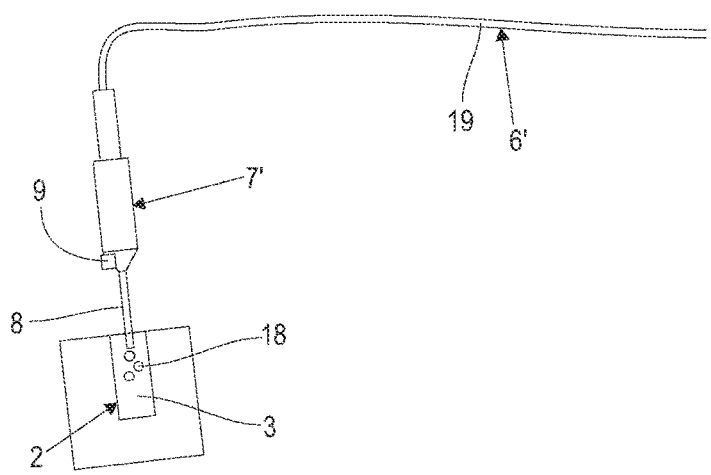
FIG. 2b illustrates an exemplary treatment handpiece fed by a delivery fiber in contact operational mode.

The handpiece 7, 7' includes an exit component 8, through which the laser beam 5 exits the delivery system 6, 6' for entering the liquid 3, as shown in FIGS. 2 and 3. The handpiece 7, 7', and in particular its exit component 8 may be configured to deliver the laser light to the liquid 3 in a contact, and/or non-contact manner. Turning now to FIG. 2a, when the treatment handpiece 7 is configured for a contact delivery, the laser light is from the said "contact" handpiece 7 directed into a "contact" exit component 8 which is configured to be at least partially immersed into the liquid 3 within the treated anatomical cavity 2 in such a manner that the laser light exits the exit component 8 within the liquid 3, at a depth of at least 1 mm, and preferably of at least 3 mm, in order to generate vapor bubbles 18 within the liquid 3, and in order the laser generated vapor bubble(s) 18 to interact with the liquid-to-cavity surface. In various embodiments, the contact exit component 8 may consist of an optical fiber tip 23 as shown in and described along with FIGS. 6a and 6b or a larger diameter exit tip 24 as shown in and described along with FIGS. 4a and 4b. In certain embodiments (FIG. 2a), the treatment handpiece 7 together with a contact exit component 8 comprises H14 tipped laser handpiece model available from Fotona, d.d. (Slovenia). And in certain embodiments, an ending of an elongated delivery fiber 19 of the laser light delivery system 6 may be immersed into the liquid 3, thus serving the function of a contact exit component 8 (FIG. 2b).

For the "contact" scenario as shown in FIGS. 2a and 2b one of the above described highly absorbed or weakly absorbed wavelengths including all other above described parameters is preferably used, thereby generating at least one vapor bubble 8 within the liquid 3. The laser system 1 further comprises a feedback system 9 to determine a bubble oscillation intensity of the at least one vapor bubble 18 generated within the liquid 3 when irradiated with the laser beam 5. The bubble oscillation intensity development and dynamics are described infra in connection with FIGS. 7, 8a and 8b. Furthermore, the laser system optionally comprises adjusting means 10 for adjusting the temporal pulse period $T_P$ (FIGS. 8a to 10) to achieve at least approximately a bubble oscillation intensity maximum. The feedback system 9 preferably comprises an acoustical, a pressure, or an optical measurement sensor for sensing the bubble oscillation period and/or intensity. As a result of the bubble oscillation intensity sensing, the temporal pulse period $T_P$ might be manually adjusted by the user. However, in a preferred embodiment, the feedback system 9 and the adjusting means 10 are connected to form a closed control loop for automatically adjusting the temporal pulse period $T_P$ to achieve the desired bubble oscillation intensity maximum.

Figure 3A:
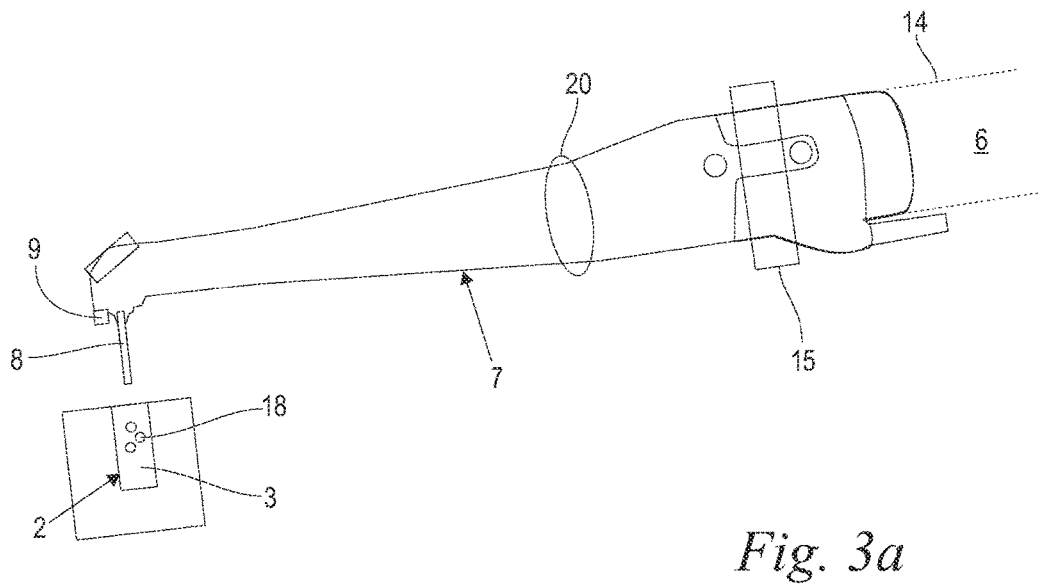
FIG. 3a illustrates an exemplary treatment handpiece fed by an articulated arm in non-contact operational mode.
Figure 3B:
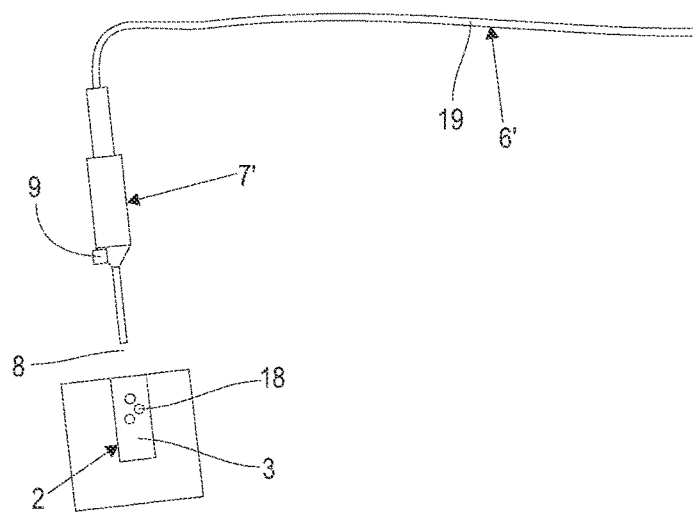
FIG. 3b illustrates an exemplary treatment handpiece fed by a delivery fiber in non-contact operational mode.

When the treatment handpiece 7, 7', and its exit component 8 are configured for a non-contact delivery (FIGS. 3a, 3b), the "non-contact" exit component 8 of the said "non-contact" handpiece 7 is configured to be positioned above the surface of the liquid 3 reservoir, with the laser energy being directed through air into the liquid 3 reservoir. In certain embodiments, a laser source 4 with a highly absorbed wavelength might be used as described above, and the exiting laser beam 5 is substantially focused onto the liquid 3 surface. In the shown "non-contact" scenario, however, preferably a laser source 4 with a weakly absorbed wavelength is used as described above, and the beam is substantially focused to a point located bellow the liquid surface by means of an appropriate focusing device, e.g. a lens system 20. The weak absorption allows the laser beam 5 to penetrate the liquid 3 until a certain penetration depth where the focal point is located. In the area of the focal point the laser energy concentration is high enough to generate the desired at least one vapor bubble 18, despite the weak absorption. In certain embodiments (FIG. 3a), non-contact treatment handpiece 7, together with a non-contact exit component 8 comprises H02 tip-less handpiece model available from Fotona, d.d. (Slovenia). And in certain embodiments, an exit component 8 consists of an ending of an elongated laser light delivery fiber 19, which is positioned above the surface of a liquid 3 reservoir (FIG. 3b). Of course, a separate exit component 8 as described along with FIG. 2a might be used for the embodiments of FIGS. 2b, 3a and 3b as well. In the alternative, and in all shown embodiments the exit component 8 can also consist of an optical exit window or a focusing optical element.

Moreover, treatment handpiece 7 may comprise any suitable components or elements configured for targeted and/or controllable delivery of laser energy to a liquid 3. Preferably, the laser system 1 comprises a scanner 15 as schematically indicated in FIGS. 2a, 3a, which allows scanning of the exit component 8 cross section with the laser beam 5, as shown in FIGS. 4a, 4b.

Turning now to FIGS. 4a, 4b, 6a, 6b, in various embodiments the exit component 8, preferably but not coercively configured for contact delivery, may consist of a fiber tip 23 (FIGS. 6a, 6b), of a larger diameter exit tip 24 (FIGS. 4a, 4b) or any other optical element, which extends along a longitudinal axis and is made of a material which is transparent to the laser beam. The exit component 8 preferably has a generally circular cross section, which leads to a generally cylindrical shape. However, any other suitable cross section may be chosen.

Figure 4A:
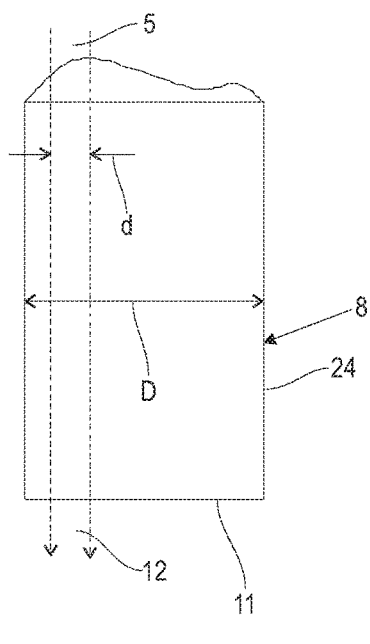
FIG. 4a illustrates an exemplary optical exit component of a treatment handpiece fed by an articulated arm, having a flat tip geometry, and showing the resultant laser beam path.

In one preferred embodiment the exit component 8 has a flat output surface 11 (FIG. 4a). The exit component 8 has a diameter D, while the laser beam 5 has a diameter d. The diameter D of the exit component 8 can be equal to the diameter of the elongated delivery fiber 19 and in particular equal to the diameter d of the laser beam 5. In the embodiment of FIG. 4a, where the exit component 8 is in the form of a larger diameter exit tip 24, the diameter D of the exit component 8 is substantially greater than the diameter d of the laser beam 5. In connection with the a.m. scanner 15 a certain scanning pattern on the flat output surface 11 can be achieved, thereby generating exiting beam portions 12 and as a result vapor bubbles 18 at corresponding locations within the liquid 3 (FIGS. 2a, 3a), as may be desired.

Figure 4B:
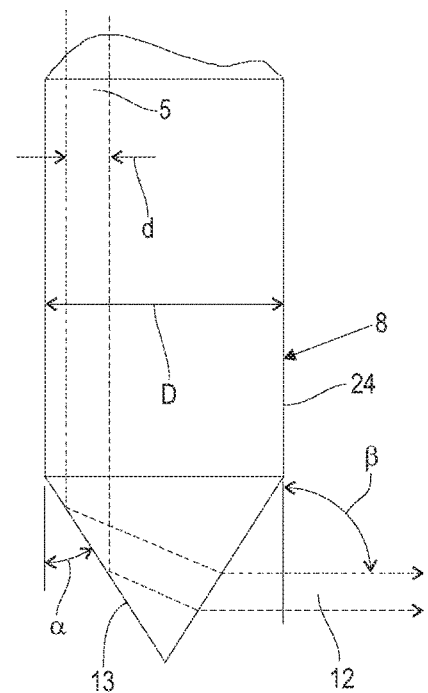
FIG. 4b illustrates an exemplary optical exit component of a treatment handpiece fed by an articulated arm, having a conical tip geometry, and showing the resultant laser beam path.

In another embodiment as shown in FIG. 4b, the exit component 8, again in the form of a larger diameter exit tip 24, has a conically shaped output surface 13 being disposed around the longitudinal axis and having an apex facing away from the incoming beam section, wherein the conically shaped output surface 13 has a half opening angle α being adapted to provide partial or preferably total reflection of the incoming beam section into a reflected beam section within the exit component 8 and to provide refraction of the reflected beam section into an exiting beam portion 12 emerging from the exit component 8 through the conically shaped output surface 13 in approximately radial direction relative to the longitudinal axis. In various embodiments, the angle β is expediently in the range $60°≤β≤120°$, and preferably about 90°.

Typically, when fiber tips 23 are used, the laser beam 5 extends substantially across the whole cross section of the fiber tip 23. This will result in a circumferentially spread exiting beam portion 12 as shown in and described below in connection with FIGS. 6a, 6b. In certain embodiments, however, as shown in FIG. 4b, the exit component 8 may have a diameter D substantially larger than the diameter d of the laser beam 5, providing space for the laser beam to be scanned over the exit component's conical output surface 13. In such embodiments, the exit component 8 base is preferably of a cylindrical shape. However, any other suitable 3D shape, such as a cube, cuboid, hexagonal prism or a cone, can be used. Scanning the conical output surface 13 with the incoming laser beam 5 allows for generation of multiple exiting beam portions 12 and corresponding vapor bubbles located circumferentially around the exit component 8. Since more than one laser pulse p, i.e. a synchronized train of pulses p (FIGS. 8b to 10) needs to be delivered to the same spot, one could deliver one pulse p exiting beam portion 12 to a related vapor bubble 18 spot, then move to the next vapor bubble 18 spot on the circumference, and so on, and then return to the same initial vapor bubble 18 spot just in time for the next pulse p within the pulse train. This would enable faster procedures since the laser repetition rate would not be limited by the bubble oscillation period $T_{bop}$ (FIGS. 8a, 8b) but by the maximum repetition rate of the laser system 1.

With reference now to FIGS. 5a, 5b, in accordance with various embodiments, when laser energy is delivered into a highly absorbing liquid 3 through an exit component 8 having a flat output surface 11 (FIG. 4a), that is immersed into the liquid 3, the above described vapor bubble 18 turns into a channel-like, extended or elongate vapor bubble 16, as shown in FIG. 5b. A channel-like bubble formation is generated also when laser energy with highly absorbed wavelength is focused in a non-contact manner onto a liquid 3 surface. On the other hand, when highly absorbed laser energy is delivered into a liquid 3 through an immersed conical output surface 13, or a flat output surface 11 of sufficient small diameter D compared to the beam diameter d, or when weakly absorbed laser energy is delivered in "non-contact" mode and focused within the liquid 3 as described above, a generally spherical vapor bubble 18 develops, as shown in FIG. 5a.

It will be appreciated that higher LA energy conversion efficiency results from the formation of spherical vapor bubbles 17. The formation of spherical vapor bubbles 17 allows for high energy punctual treatment. On the other hand, the formation of elongate vapor bubbles 16 allows for an extended treatment depth even in complex and or narrow cavities 2 with poor access for the exit component 8. Moreover, the difference in the shape of vapor bubbles, and correspondingly in the conversion efficiency, of flat and conically shaped fiber tips, starts to diminish when laser beam diameters smaller than approximately 300 µm are being used.

With reference now to FIGS. 6a, 6b, a comparison of numerically calculated laser beam characteristics, out of a conically shaped fiber tip 23 are illustrated, depending on whether the laser light delivery system 6' comprises an elongate delivery fiber 19 (FIGS. 2b, 3b, 6a), or the laser light delivery system 6 comprises an articulated arm 14 (FIGS. 2a, 3a, 6b). Both exit components 8 of FIGS. 6a, 6b are geometrically identical, and are subjected to a full cross section laser irradiation. Calculations were made for a particular embodiment with an Er:YAG laser wavelength of 2940 nm, and a fiber tip 23 cone made out of quartz, with a conical half angle α=35.5 degrees. However the difference in beam distributions depending on the type of the delivery system 6, 6' used, applies also to other wavelengths, and fiber tip 23 parameters. Due to different optical transmission properties of the two types of the optical delivery system 6, 6', the angular distribution of a laser beam's 5 exiting beam portion 12 coming out of an elongated delivery fiber 19 is much broader than when coming out of an articulated arm 14 where the laser beam 5 remains approximately collimated. Therefore, when a laser beam 5 is delivered to a conically shaped output surface 13 by an elongate delivery fiber 19 (FIG. 6a), the angular distribution of the laser beam's 5 exiting beam portion 12 coming out of the output surface 13 remains relatively broad and omnidirectional. On the other hand, when a laser beam 5 is directed into a conically shaped output surface 13 from an articulated arm 14 (FIG. 6b), the laser beam's 5 exiting beam portion 12 coming out of the fiber tip 23 cone is substantially concentrated within a circular ring which is distributed in a radial direction around the said cone. It will be appreciated that a radially unidirectionally distributed exiting beam portion 12 as obtained with an articulated arm 14 (FIG. 6b), is more suitable for generating highly efficient spherical vapor bubbles 17, in comparison to the relatively more omnidirectional exiting beam portion 12 as obtained with an elongate fiber 19 optical delivery used in the aforementioned prior art of FIG. 6a.

It should be noted that for highly absorbed wavelengths, typically a lower LA energy conversion efficiency is obtained in a non-contact than in a contact manner. This is because when a highly absorbed wavelength is delivered onto a liquid 3 in a non-contact manner, the vapor bubble 18 gets formed immediately at, or substantially close to the liquid-to-air surface boundary. The bubble's energy can therefore, at least partially, get released into easily compressible air, instead of into hardly compressible liquid. This explains why the aforementioned prior art method requires that the laser energy to be delivered into the root canal in a "contact" manner, by means of a fiber tip which is to be substantially completely immersed into a liquid. However, using an inventive laser pulse sequence described herein, vapor bubbles 18 extending deeper into the liquid, and away from the liquid-to-air surface boundary, can be formed, resulting in a substantially increased LA energy conversion efficiency.

Moreover, it is to be appreciated, that when in certain embodiments a weakly absorbed laser beam is delivered to a liquid 3 in a non-contact manner, and the beam's focus is located within the liquid 3, and away from the liquid surface, no bubble gets formed at or near the liquid's surface. Instead, the beam gets transmitted deeper into the liquid, and providing that the pulse duration is sufficiently short (≤85 ns), and the power density at the focal point within the liquid is sufficiently high, a bubble 18 is generated only when the laser beam 5 reaches its focal point deeper within the liquid 3. From the viewpoint of bubble dynamics, such an embodiment is comparable in its effect to an embodiment where a highly absorbed wavelength is delivered to a liquid 3 in a contact manner. High LA conversion efficiencies can therefore be obtained also in a non-contact manner, providing that high power, weakly absorbed laser beams are used.

Turning now to FIG. 7, in various embodiments, the system utilizes an improved scientific understanding of the interaction of pulsed laser light with a highly absorbing liquid 3. When a pulsed laser beam 5 according to the present invention is delivered to such a liquid 3 at a time $t_0$, a bubble oscillation sequence develops. In the 1st phase of the bubble oscillation sequence (from time $t_0$ to time $t_{max1}$), laser energy deposition into the liquid 3 via absorption causes superheating of the liquid 3, and boiling induces a vapor bubble 18. In this $1^{st}$ phase, stress waves are typically not induced within the liquid 3. The vapor bubble 18 expands rapidly, and thereafter reaches its maximum size at $t_{max1}$, when the internal pressure matches the pressure in the surrounding liquid 3.

In the $2^{nd}$ phase (from time $t_{max1}$ to time $t_{min1}$), the internal pressure is lower than the pressure in the surrounding liquid 3, and this difference in pressures forces the vapor bubble 18 to collapse. During the collapse, a portion of the energy stored in the vapor bubble 18 is converted into acoustic energy. This results in the emission of acoustic transients, which are sometimes in the form of shock waves. When the liquid 3 medium is contained in a root canal, i.e. in a body cavity 2 as shown in FIGS. 2a, 2b 3a, 3b, the acoustic transients produce irrigation, including debriding, cleaning, decontamination, rinsing, and/or sterilization effects within the liquid filled body cavity 2.

When the vapor bubble 18 collapse completes at time $t_{min1}$, a rebound occurs thereafter, and the vapor bubble 18 starts to grow again up until time $t_{max2}$. This $3^{rd}$ phase (from time $t_{min1}$ to time $t_{max2}$) is followed again by a collapse in the $4^{th}$ phase (from time $t_{max2}$ to time $t_{min2}$). This oscillation process of the vapor bubble 18 continues, decreasing in amplitude and temporal period each time as illustrated in FIG. 7, and new acoustic transients are emitted after each collapse.

In various embodiments, a temporal bubble oscillation period $T_{bop}$ may be defined as the time between $t_o$ and $t_{min1}$. Temporal bubble oscillation period $T_{bop}$ may vary based at least in part on the thermo-mechanical properties of the liquid 3, the shape and volume of the liquid 3 reservoir, the laser beam 5 emission profile, and so forth. Accordingly, in various embodiments, temporal bubble oscillation period $T_{bop}$ may be modified, as suitable, based on adjustments of these or other parameters.

Measurements of vapor bubble 18 formation in a boundless water reservoir under Er:YAG laser pulses of durations from about 15 microseconds (µs) to about 180 µs, pulse energies from about 5 mJ to about 100 mJ, and exit component 8 diameters from 300 µm to 600 µm, result in oscillation periods $T_{bop}$ in the range from 120 µs to 580 µs, and therefore in bubble oscillation frequencies $f_b=1/T_{bop}$ in the range of 1.7 kHz to 8.3 kHz. The temporal bubble oscillation period $T_{bop}$ is longer for longer pulse p durations during which laser energy continues to be delivered while the vapor bubble 18 is expanding. Measurements show, in agreement with Eq. 3, that the LA energy conversion efficiency η to be higher for higher laser pulse energies and shorter pulse durations. The increase in η is particularly pronounced when pulse durations shorter than 250 µs, and preferably shorter than 120 µs are used. For example, for a 400 µm diameter conical fiber tip, and Er:YAG laser pulse energy of 20 mJ, η in water was observed to increase from about η=0.04 at 120 µs to about η=0.14 at 60 µs, and to about η=0.48 at 25 µs. The LA conversion efficiency was also observed to be by a factor of about 3 higher with a conical than with a flat fiber tip. It is to be noted that in various embodiments the bubble oscillation time and LA efficiency will depend also on other parameters, such as the temperature and chemical and physical characteristics of the liquid, cavity's shape and dimensions, handpiece exit component geometry, laser beam dimensions and other characteristics, etc. Therefore, oscillation periods may be within a range from 1 kHz to 10 kHz.

The foregoing vapor bubble 18 oscillation dynamics and associated relation to laser-to-bubble energy efficiency facilitate the improved inventive system for and methods of treatment utilizing delivery of laser pulses p, for example treatment of root canals, drilled bone, and/or the like anatomical cavities 2.

In various inventive embodiments wherein improved LA energy conversion efficiency is sought, principles of the present disclosure contemplate use of laser pulses p having a pulse duration $t_p$ shorter than about 250 µs, and preferably shorter than 120 µs. Additionally, when improved conversion efficiency is desired, the laser emission profile may desirably be formed by a conically shaped fiber tip, and/or the diameter of a flat fiber tip; or when the laser beam with a highly absorbed wavelength is delivered onto a liquid's surface in a non-contact manner, the laser beam spot size at the liquid surface may desirably be smaller than about 300 μm.

Figure 8A:
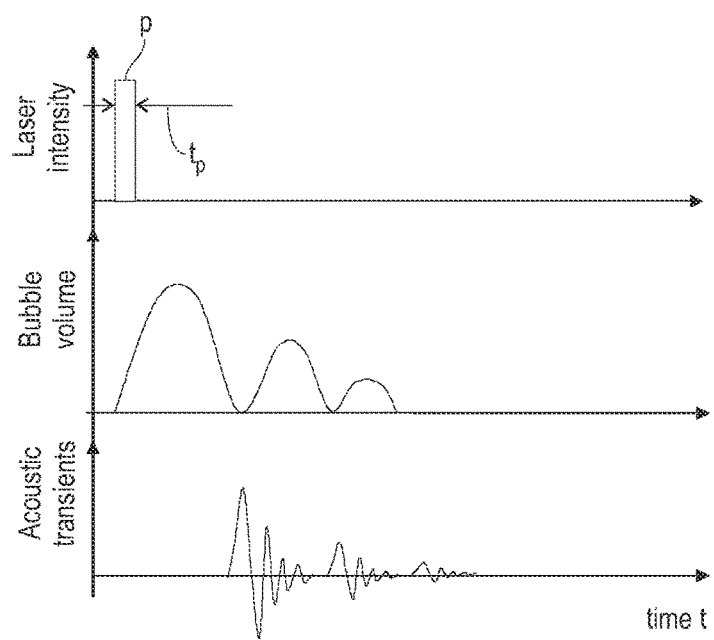
FIG. 8a illustrates an exemplary development of vapor bubbles and acoustic transients sequence following a laser pulse according to the prior art.
Figure 8B:
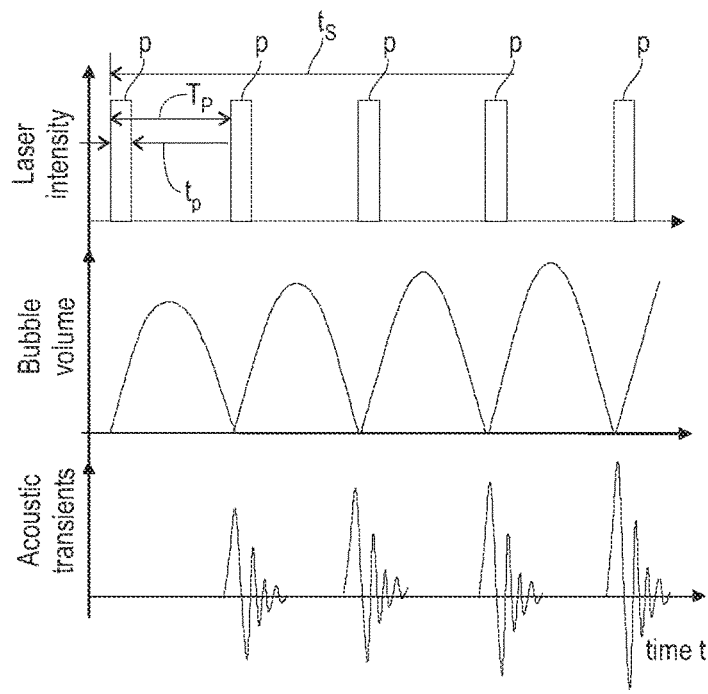
FIG. 8b illustrates an exemplary sequence of laser pulses, vapor bubbles and acoustic transients, according to the present invention.

Moreover, and referring now to FIGS. 8a, 8b, in various embodiments, LA energy conversion efficiency can be enhanced, and the duration of acoustic transients may be prolonged by delivering laser pulses p in a sequence that is synchronized with the bubble oscillation period $T_{bop}$, in order to achieve at least approximately a bubble oscillation intensity maximum. It is to be appreciated that illustrations in FIGS. 8a, 8b are made only for the purposes of describing the invention, and do not necessarily depict amplitudes and shapes of laser pulses, bubble volumes or acoustic transients, as would be observed in actual embodiments of the invention.

The temporal dynamics of the generated bubbles and acoustic transients according to the prior art are shown in FIG. 8a. It is to be appreciated that without the below described inventive laser-to-bubble synchronization, and when the laser pulse energy is optimized to be just above the level required to achieve the irrigation effect, it is only the acoustic transients resulting from the bubble collapse during the $2^{nd}$ phase that are sufficiently strong to produce effective irrigation, including debriding, cleaning and decontamination of an anatomical cavity. The energy of the acoustic transients which are released as a result of bubble collapses during the $4^{th}$ and subsequent phases, is therefore wasted, and contributes mainly to a further heating of the liquid.

On the other hand, FIG. 8b shows the inventive laser pulse sequence with pulse durations $t_p$ and inventive temporal pulse period $T_P$, and the resulting dynamics of the resulting vapor bubbles and acoustic transients. Individual pulses p within one sequence follow each other by a pulse period $T_P$. When within the inventive pulse sequence the temporal pulse period $T_P$ is adjusted such, that a subsequent laser pulse p is delivered slightly before or at the time the vapor bubble formed by a prior laser pulse p has just collapsed (i.e., at about time $t_{min1}$), the bubble energies of the two laser pulses p are resonantly enhanced. In addition, since the second vapor bubble, resulting from the second laser pulse p, will begin formation when the first vapor bubble resulting from the previous laser pulse p, is already small or absent, the second vapor bubble will develop in space significantly not affected by the previous laser pulse p. Stated differently, by synchronizing laser pulses p and their temporal pulse period $T_P$ to a bubble oscillation period $T_{bop}$, potentially conflicting and/or undesirable interactions between vapor bubbles may be reduced and/or minimized, resulting in improved shockwave generation, magnitude, and/or efficacy.

In summary and opposite to the prior art pulse sequence and vapor bubble formation, when the inventive synchronization is applied, the bubble's energy following each laser pulse is enhanced by the remaining bubble's energy from the prior pulse. As a result, the volume of the generated bubbles during a laser pulse sequence starts to increase with each subsequently delivered laser pulse p, resulting in effective acoustic transients following each bubble collapse. Numerical simulations show that bubble's energy will increase from pulse p to pulse p for the first three to eight pulses p in a sequence, after which the bubble's energy will stabilize at the enhanced value. Moreover, the inventive synchronization results in a prolonged duration of acoustic transients, potentially significantly increasing the kill rate of bacteria within the treated cavity 2.

In one set of our experiments, two to four consecutive Er:YAG (2.94 μm) pulses with the pulse duration $t_p$, in the range of 15 to 50 μs, and single pulse energies from 5 mJ to 20 mJ, were delivered to a water filled experimental model of a root canal through fiber tips with their endings submersed in water to a depth of 2-6 mm. Conical and flat fiber tips with diameters of about 300 μm, 400 μm, 500 μm and 600 μm were used. The conical half angle α of the conical tips was about 18 deg. Depending on the specific fiber tip used, and the pulse energy, the above described inventive synchronization of laser pulses p to the bubble oscillation period $T_{bop}$ was observed to occur when the temporal pulse period $T_P$ was set to 180 μs≤$T_P$≤460 μs, for the conical fiber tips, and to 120 μs≤$T_P$≤340 μs for the flat ended fiber tips.

It is to be understood that for bubbles with small dimensions in comparison with the dimensions of the anatomical cavity, the optimal temporal pulse period $T_P$ will be fixed for a chosen combination of the laser wavelength, laser pulse energy, type of the liquid, optical delivery and exit component configuration, and other conditions. In such a case, no feedback or adjusting means would be required to perform the inventive irrigation method. For example, for the Er:YAG laser pulse duration of 25 μs, pulse energy of 20 mJ, and fiber tip diameter of 400 μm, the bubble oscillation period $T_{bop}$ in a large water reservoir, and therefore the optimal temporal pulse period $T_P$, was found to be fixed at about 350 μs for the conical tip, and at about 250 μs for the flat-ended tip.

Said synchronization by the inventive adjustment of the temporal pulse period $T_P$ to achieve at least approximately a bubble oscillation intensity maximum can be achieved in different ways. One preferred way both in terms of system and method is, that the feedback system 9 is adjusted to determine the bubble oscillation period $T_{bop}$ of the liquid 3 when irradiated with the laser beam 5, wherein the adjusting means 10 are adapted to adjusting the temporal pulse period $T_P$ for at least approximately matching the bubble oscillation period $T_{bop}$. In this case the pulse period $T_P$ is further adjusted to be in the range from about 100 μs to about 1000 μs, and preferably from about 120 μs to about 580 μs.

In certain instances, it may be desirable to have bubbles form with a channel-like shape, for example in order to extend deeper into an anatomical crevice such as a root canal. Bubbles extending deeper into the liquid are desirable also when laser energy with a highly absorbed wavelength is delivered onto the liquid in a non-contact manner. This is due to the fact that a bubble's collapse at or close to the water-to-air surface boundary does not result in sufficiently strong acoustic transients. Accordingly, in such or other cases, the laser system 1 and the related method may be configured to deliver laser pulses at half the oscillation period $T_{bop}/2$. The adjusting means 10 are therefore adapted to adjusting the temporal pulse period $T_P$ for at least approximately matching one half of the bubble oscillation period $T_P=T_{bop}/2$. The pulse period $T_P$ is further adjusted to be in the range from about 50 μs to about 500 μs, and preferably from about 60 μs to about 290 μs. In other words, laser system 1 may deliver a subsequent laser pulse p at the time when a prior vapor bubble reaches, or is close to, its maximum volume. In these instances, the vapor bubble is primarily laser-pulse driven rather than vapor driven, because the bulk of the energy of the subsequent laser pulse passes through the vapor bubble and is absorbed at the vapor bubble wall area generally opposite to the direction of the laser beam, thus extending the length of the vapor bubble in the direction of laser beam emission, and away from the liquid-to-air surface boundary. This approach may be desirable, for example, when a highly absorbed wavelength is delivered to a liquid in a non-contact manner. By extending the bubble deeper into the liquid, and away from the liquid surface, the potential loss of the bubble's energy into the surrounding air may be significantly reduced.

In both aforementioned cases, and according to a preferred embodiment of the invention, the feedback system 9 and the adjusting means 10 are connected to form a closed control loop for automatically adjusting the temporal pulse period $T_P$ to achieve the described synchronization of the laser pulses p with the vapor bubble generation as indicated by their bubble oscillation period $T_{bop}$. However, a manual user adjustment of the temporal pulse period $T_P$ to the bubble oscillation period $T_{bop}$ might be contemplated as well within the scope of the invention.

The aforementioned synchronization applies to one single treatment spot only, where a single oscillating bubble, or a train of such bubbles is sought to be generated by a synchronized train of pulses p. In case of desired simultaneous multiple bubble generation as is inventively possible along with the use of a scanner 15 (FIGS. 4A, 4B), the pulse repetition rate=1/temporal pulse period $T_P$ needs to be multiplied by the number of individual bubble generation spots. In result the inventive synchronization of approximately $T_P=T_{bop}$ or $T_P=T_{bop}/2$ applies for each individual bubble generation spot while the inventive laser pulse repetition rate may be higher. Higher pulse repetition rates may be of benefit when higher energy efficiency of the laser source 4 is desired. In particular, when laser pulses can be made to follow each other with a temporal pulse period which is shorter than the inversion population time of a particular laser active material of a laser source 4, this will result in a significantly increased lasing efficiency.

In contrast to prior art approaches, the inventive laser pulse repetition rates are much higher. For example, laser system 1 utilizes laser pulse repetition rates from about 1 kHz to about 20 kHz, or even higher when a scanner is used; in contrast, prior approaches utilized laser pulse repetition rates from about 2 Hz to about 25 Hz.

Referring now simultaneously to FIG. 1 to 10, the inventive laser system 1 is proposed, comprising a laser source 4 for generating a laser beam and a control unit, wherein a wavelength of the laser beam is in a range from above 0.4 µm to 11.0 µm inclusive, and wherein the laser system 1 including the control unit 22 is adapted for irrigation, including debriding, cleaning and decontamination of anatomical cavities 2 such, that the laser source 4 is being operated in pulsed operation wherein individual pulses p (FIGS. 8, 10) of the laser source 4 or of a laser beam 5 generated by the laser source 4 are combined to pulse sets 21 as explained infra in connection with FIGS. 9 and 10. In order to facilitate improved adjustability and/or control, in various embodiments the laser system 1 is configured with a laser source 4 having a variable pulse rate, variable pulse set rate, and variable temporal pulse set length $t_S$ of the pulse set 21. In this manner, the LA energy conversion efficiency and the duration of acoustic transients may be optimized for a particular anatomical cavity 2 dimensions and shape. Additionally, the vapor bubble 18 shape is controllable by changing the pulse period $T_P$ over a range between about the full bubble oscillation period $T_{bop}$ and half oscillation period $T_{bop}$.

FIG. 9 shows in a schematic diagram the temporal course of the pulse sets 21 according to the invention. In this connection, the course of the amplitude of the pulse sets 21 is illustrated as a function of time. The pulse sets 21 follow one another along one single optical path within the laser system 1 with a temporal pulse set spacing $T_S$ being the temporal difference between the end of one pulse set 21 and the beginning of the next pulse set 21. The temporal pulse set spacing $T_S$ is expediently 20 ms≤$T_S$≤500 ms, advantageously 20 ms≤$T_S$≤100 ms, and is in the illustrated embodiment of the inventive method approximately 20 ms. The lower temporal limit for temporal set spacing $T_S$ of 20 ms is set in order to allow sufficient time for the laser active material, such as, for example, a flash-lamp pumped laser rod, to cool off during the time between subsequent pulse sets 21. The individual pulse sets 21 have a temporal set length $t_S$ of, for example, approximately 2 ms. Depending on the number of individual pulses p provided infra the value of the temporal set length $t_S$ can vary. The maximal number of pulse sets 21, and correspondingly the maximal number of individual pulses p, that may be delivered during a treatment is limited at least by the maximal delivered cumulative energy below which the temperature increase of the liquid 3 does not exceed an allowed limit.

FIG. 10 shows an enlarged detail illustration of the diagram according to FIG. 9 in the area of an individual pulse set 21. Each pulse set 21 has expediently at least two and maximally 20 individual pulses p, advantageously two to eight individual pulses p, and preferably three to six individual pulses p, and in the illustrated embodiment according to FIG. 10 there are seven individual pulses p. Maintaining the aforementioned upper limit of the number of individual pulses p per pulse set 21 avoids overheating of the laser active material. The individual pulses p have a temporal pulse length $t_p$ and follow one another along one single optical path within the laser system in a temporal pulse period $T_P$, the temporal pulse period $T_P$ being the time period from the beginning of one single pulse p to the beginning of the next, subsequent pulse p, the pulse repetition rate $f_P$ therefore being equal to $f_P=1/T_P$.

The pulse length $t_p$ is for weakly absorbed wavelengths in the range of ≥1 ns and <85 ns, and preferably ≥1 ns and ≤25 ns. The lower temporal limit of the pulse length $t_p$ for weakly absorbed wavelengths ensures that there are no shock waves created in the liquid 3 during the vapor bubble 18 expansion. And the upper pulse length $t_p$ limit for weakly absorbed wavelengths ensures that the laser pulse power is sufficiently high to generate optical breakdown in the liquid.

For highly absorbed wavelengths, the pulse length $t_p$ is in the range of ≥1 µs and <250 µs, and preferably of ≥1 µs and <120 µs. The lower temporal limit for highly absorbed wavelengths ensures that there is sufficient pulse energy available from a free-running laser. And the upper pulse duration limit for highly absorbed wavelengths ensures that the generated heat does not spread via diffusion too far away from the vapor bubble, thus reducing the LA energy conversion efficiency. Even more importantly, the upper pulse duration limit ensures that laser pulses are shorter than the vapor bubble rise time, $t_{max1}-t_0$, in order not to interfere with the bubble temporal oscillation dynamics. In FIG. 10, the amplitude of the laser beam or of its individual pulses p is schematically plotted as a function of time wherein the temporal course of the individual pulses p, for ease of illustration, are shown as rectangular pulses. In practice, the pulse course deviates from the schematically shown rectangular shape of FIG. 10.

The pulse period $T_P$ is, according to the invention, in the range between approximately $T_{bop}/2$ and approximately $T_{bop}$. The bubble oscillation period $T_{bop}$ may vary from about 100 µs to about 1000 µs, based at least in part on the thermo-mechanical properties of the liquid 3, the shape and volume of the liquid reservoir, the laser wavelength, beam emission profile, configuration of the treatment head, and so forth. Accordingly, when the pulse period $T_P$ will be adjusted to approximately match $T_{bop}$, the pulse repetition rate $f_P$, will be in the range from about 1 kHz to about 10 kHz, and preferably from about 1.7 kHz to about 8.3 kHz, corresponding to a pulse period $T_P$ in the range from about 100 μs to about 1000 μs, and preferably from about 120 μs to about 580 μs. And when the pulse period $T_P$ will be adjusted to approximately match $T_{bop}/2$, the pulse repetition rate $f_P$, will be in the range from about 2 kHz to about 20 kHz, and preferably from about 3.4 kHz to about 16.6 kHz, corresponding to a pulse period $T_P$ in the range from about 50 μs to about 500 μs, and preferably from about 60 μs to about 290 μs. Accordingly, in various embodiments, pulse period $T_P$ may be modified, as suitable, based on adjustments of these or other parameters. For illustration purposes only, the pulse period $T_P$ is chosen in FIG. 10 as an example to be 200 μs.

The laser pulse energy $E_L$, according to the invention, may be fixed for all pulses within a pulse set 21. In certain embodiments, however, the pulse energy may be adjustable to automatically gradually decrease, for example linearly or exponentially, from pulse p to pulse p within each set 21, in order to compensate for the gradual increase in the LA energy conversion efficiency from pulse p to pulse p. The pulse energy may be adjusted to gradually, for example linearly or exponentially, decrease from the first to the $N^{th}$ pulse 1 within each pulse set 21, where N is ≥3 and ≤8, however not larger than the number M of all pulses p within each set 21.

Alternatively, the laser pulse energy $E_L$, may be adjustable to gradually increase from pulse to pulse p within a pulse set 21, in order to increase even further the amplitude of the acoustic transients, already enhanced by the laser-to-bubble synchronization.

Corresponding to the above described inventive laser system 1, and with reference to all FIGS. 1 to 10, a related method for irrigation, including debriding, cleaning and decontamination, of anatomical cavities 2 filled liquid 3 comprises the following steps:
providing a laser system 1 comprising a laser source 4 for generating a laser beam 5, an optical delivery system 6, a treatment handpiece 7 including an exit component 8, a feedback system 9 and adjusting means 10, wherein the treatment handpiece 7 and its exit component 8 are configured to irrigate the anatomical cavity 2 in a contact or non-contact manner, wherein a wavelength of the laser beam 5 is in a range from above 0.4 μm to 11.0 μm inclusive, wherein the laser system is adapted to be operated in pulsed operation with pulse sets 21 containing at least two and maximally twenty individual pulses p of a temporally limited pulse length $t_p$, wherein the temporal separation $t_s$ between the pulse sets is ≥20 ms, and wherein the individual pulses p follow one another with a temporal pulse period $T_P$ within a range of 50 μs, inclusive, to 1000 μs, inclusive,
applying said pulsed laser beam 5 to the liquid 3 disposed within the anatomical cavity 2 to form at least one vapor bubble 18 in the liquid 3;
determining a bubble oscillation intensity of the vapor bubble 18 within the liquid 3 when irradiated with the laser beam 5 by means of the feedback system 9,
adjusting the temporal pulse period $T_P$ of the laser beam 5 to achieve at least approximately a bubble oscillation intensity maximum,
performing the treatment until desired irrigation, including debriding, cleaning and decontamination, is achieved, or until the temperature rise within the anatomical cavity does not exceed 3.5 degrees Celsius, whichever occurs first.

Preferably, the feedback system 9 and the adjusting means 10 are connected to form a closed control loop, and wherein the temporal pulse period $T_P$ is automatically adjusted by said closed control loop to achieve at least approximately said bubble oscillation intensity maximum. The bubble oscillation intensity is expediently sensed by an acoustical, a pressure, or an optical measurement sensor of the feedback system 9.

The method my comprise the steps of determining by means of the feedback system 9 a bubble oscillation period $T_{bop}$ of the liquid 3 when irradiated with the laser beam 5, adjusting by means of the adjusting means 10 the temporal pulse period $T_P$ for at least approximately matching the bubble oscillation period $T_{bop}$, and further adjusting the pulse period $T_P$ to be in the range from about 100 μs to about 1000 μs, and preferably from about 120 μs to about 667 μs.

Alternatively, the method my comprise the steps of determining by means of the feedback system 9 a bubble oscillation period $T_{bop}$ of the liquid 3 when irradiated with the laser beam 5, adjusting by means of the adjusting means 10 the temporal pulse period $T_P$ for at least approximately matching one half of the bubble oscillation period $T_{bop}$, and further adjusting the pulse period $T_P$ to be in the range from about 50 μs to about 500 μs, and preferably from about 63 μs to about 333 μs.

A wavelength of the laser beam 5 may be chosen such that the laser beam 5 is highly absorbed in the liquid 3, wherein the laser pulse duration is in the range of ≥1 μs and <250 μs, and preferably of ≥1 μs and <120 μs. In particular, the liquid 3 is OH-containing, and wherein as a laser source 4 one of an Er:YAG laser having a wavelength of 2940 nm, an Er:YSGG laser having a wavelength of 2790 nm, an Er,Cr:YSGG laser having a wavelength of 2780 nm or 2790 mm, or a $CO_2$ laser having a wavelength of 9300 to 10600 nm is used, and wherein the energy of an individual laser pulse p is in a range from 1 mJ to 100 mJ. Preferably, the laser source is an Er:YAG laser having a wavelength of 2940 nm, wherein the laser pulse energy is in a range from 1.0 mJ to 40.0 mJ, and preferably within a range from 5.0 mJ to 20.0 mJ.

In a preferred embodiment, the exit component 8 of the handpiece 7 has a flat output surface 11 and provides a generally parallel exiting beam portion 12 of the laser beam 5, wherein the flat output surface 11 is disposed in a distance to the liquid 3 within the anatomical cavity 2, and wherein by means of the handpiece 7 and its exit component 8 the laser energy is delivered to the liquid 3 within the anatomical cavity 2 in a non-contact manner, thereby generating an elongate vapor bubble 16 in the liquid 3.

Alternatively, the exit component 8 of the handpiece 7 has a flat output surface 11 and provides a generally parallel exiting beam portion 12 of the laser beam 5, wherein the flat output surface 11 is immersed in the liquid 3 within the anatomical cavity 2, and wherein by means of the handpiece 7 and its exit component 8 the laser energy is delivered to the liquid 3 within the anatomical cavity 2 in a contact manner, thereby generating either one of an elongate vapor bubble 16 or a spherical vapor bubble 17 in the liquid 3.

In a further alternative, the exit component 8 of the handpiece 7 has a substantially conically shaped output surface 13 and provides a generally circumferentially spread exiting beam portion 12 of the laser beam 5, wherein the conically shaped output surface 13 is immersed in the liquid 3 within the anatomical cavity 2, and wherein by means of the handpiece 7 and its exit component 8 the laser energy is delivered to the liquid 3 within the anatomical cavity 2 in a contact manner, thereby generating a generally spherical vapor bubble 17 in the liquid 3. Preferably, the delivery system 6 comprises an articulated arm 14, and wherein the laser beam 5 is delivered from the laser source 4 to the conically shaped output surface 13 through the articulated arm 14.

The wavelength of the laser beam 5 may alternatively chosen such that the laser beam 5 is weakly absorbed in the liquid 3, wherein the laser pulse duration is in the range of ≥1 ns and <85 ns, and preferably of ≥1 ns and <25 ns. In particular, the liquid 3 is OH-containing, and wherein as a laser source 4 one of a Q-switched Nd:YAG laser source having a wavelength of 1064 nm, a Q-switched ruby laser source having a wavelength of 690 nm, or an alexandrite laser source having a wavelength of 755 nm is used, including laser sources 4 with frequency doubled wavelengths of these laser sources.

Preferably, optical focusing means 16 are provided, wherein the exit component 8 of the handpiece 7 is disposed in a distance to the liquid 3 within the anatomical cavity 2, and wherein by means of the optical focusing means 16 the laser energy is focused in the liquid 3 within the anatomical cavity 2, thereby delivering the laser energy to the liquid 3 in a non-contact manner, and thereby generating a generally spherical vapor bubble 17 in the liquid 3.

Expediently, the delivery system 6 further comprises a scanner 15, and wherein one of a flat shaped output surface 11 and a conically shaped output surface 13 of the exit component 8 is scanned with the incoming laser beam 5 by means of the scanner 15.

The pulse set 21 may consist of two to eight individual pulses p, and preferably of three to six individual pulses p. One pulse set 21 has a temporal pulse set length $t_S$, and wherein the temporal set length $t_S$ may be >100 μs, and preferably >1000 μs. The energy of laser pulses p within a pulse set may be adjusted by one of the user or a control system of the laser system 1 to gradually decrease linearly or exponentially from the first to the $N^{th}$ pulse within each pulse set, where N is ≥3 and ≤8, however not larger than the total number of pulses p within each set.

In a further aspect of the invention, the inventive method for irrigation, including debriding, cleaning and decontamination, of liquid filled anatomical cavities 2 may comprise the steps of:
  providing a laser system 1 comprising a laser source 4 for generating a laser beam 5, an optical delivery system 6, a treatment handpiece 7 including an exit component 8, wherein optical delivery system 6 comprises an articulated arm 14, wherein the handpiece 7 and its exit component 8 are configured to irrigate the anatomical cavity 2 in a contact manner, wherein the exit component 8 has a conical output surface 13, wherein a wavelength of the laser beam 5 is in a range from above 0.4 μm, inclusive, to 11.0 μm inclusive, wherein the laser system 1 is adapted to be operated in pulsed operation with pulse sets 21 containing at least one and maximally twenty individual pulses p of a temporally limited pulse length $t_p$, wherein the laser pulse length $t_p$ is in the range of ≥1 μs and <250 μs, preferably in the range of ≥1 μs and <120 μs, and wherein a temporal separation $T_S$ between the pulse sets 21 is ≥20 ms.
  applying said pulsed laser light in a contact manner to a liquid 3 disposed in the anatomical cavity 2 thereby forming a vapor bubble 18; and
  performing the treatment until desired irrigation, including debriding, cleaning and decontamination, is achieved, or until the temperature rise within the anatomical cavity does not exceed 3.5 degrees Celsius, whichever occurs first.

Expediently, the laser system 1 is configured to generate coherent light having a wavelength highly absorbed in OH-containing liquids, by means of one of an Er:YAG laser source having a wavelength of 2940 nm, an Er:YSGG laser source having a wavelength of 2790 nm, an Er,Cr:YSGG laser source having a wavelength of 2780 nm or 2790 nm, and a $CO_2$ laser source having a wavelength of about 9300 to about 10600 nm, and wherein laser pulse energy is in a range from 1 mJ to 100 mJ.

Preferably, the laser source 4 is an Er:YAG laser source having a wavelength of 2940 nm, wherein laser pulse energy is in a range from 1 mJ to 40 mJ, wherein the exit component 8 is cylindrical, having a diameter D between 200 μm and 1000 μm, wherein the conical output surface 13 has a conical half angle α being in the range from 16° to 38°, preferably from 34° to 38°, wherein the temporal separation $T_S$ between pulse sets 21 is <0.5 s, and wherein the cumulative delivered energy during a treatment is below 150 J.

It will be appreciated that, while the foregoing example methods are directed to treatment of root canals and/or bone cavities, in accordance with principles of the present disclosure, similar methods and/or systems may be utilized to treat other body tissues, for example periodontal pockets, and/or the like. The method may be also used to irrigate, debride and clean selected small surfaces of electronic and precision mechanical components during manufacturing, maintenance and servicing, especially when it is not desirable or possible to expose the whole electronic or other component to a standard cleaning or irrigation procedure.

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure and may be expressed in the following claims. The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element of any or all the claims.

Systems, methods and computer program products are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection. When language similar to "at least one of A, B, or C" is used in the claims, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

The specification incorporates by reference the entire disclosure of European priority patent application EP 14 000 529.9 having a filing date of Feb. 13, 2014.

While specific embodiments of the invention have been shown and described in detail to illustrate the inventive principles, it will be understood that the invention may be embodied otherwise without departing from such principles.

What is claimed is:

1. Dental irrigation system being configured for irrigation, including debriding, cleaning and decontamination, of open tooth cavities (2) filled with a liquid (3), the irrigation system comprising a laser system (1), wherein the laser system (1) comprises a laser source (4) for generating a laser beam (5) and an optical delivery system (6) for the laser beam (5), wherein the delivery system (6) includes a treatment handpiece (7) and an exit component (8), wherein the treatment handpiece (7) and the exit component (8) are configured to irradiate a liquid (3) within the open tooth cavity (2) with the laser beam (5), wherein a wavelength of the laser beam (5) is in a range from above 0.4 µm to 11.0 µm inclusive, wherein the laser system (1) is adapted to be operated in pulsed operation with pulse sets (21) containing at least two and maximally twenty individual pulses (p) of a temporally limited pulse length ($t_p$), wherein the pulse sets (21) follow one another with a temporal separation ($T_s$), and wherein the individual pulses (p) follow one another with a pulse repetition rate ($f_p$), wherein the laser system is adapted to generate at least one vapor bubble (18) within the liquid (3) when irradiated with the laser beam (5), wherein one single pulse (p) causes the at least one vapor bubble (18) to oscillate between a maximal and a minimal volume with a bubble oscillation frequency ($f_b$), and wherein the pulse repetition rate ($f_p$) of the individual pulses (p) within one pulse set (21) is adjusted relative to the bubble oscillation frequency ($f_b$) such, that a synchronization between the delivery of the pulses (p) and the bubble oscillation is achieved.

2. The dental irrigation system according to claim 1, wherein the pulse repetition rate ($f_p$) is adjusted to be in a range from about 1 kHz to about 20 kHz.

3. The dental irrigation system according to claim 1, wherein the temporal separation ($T_s$) between the pulse sets is ≥20 ms.

4. The dental irrigation system according to claim 1, wherein the pulse repetition rate ($f_p$) is adjusted to be at least approximately equal to the bubble oscillation frequency ($f_b$), thereby delivering the pulses (p) synchronized to the presence of a bubble oscillation intensity minimum.

5. The dental irrigation system according to claim 1, wherein the pulse repetition rate ($f_p$) is adjusted to be at least approximately equal to the double of the bubble oscillation frequency ($f_b$), thereby delivering the pulses (p) synchronized to the presence of a bubble oscillation intensity minimum and a bubble oscillation intensity maximum in an alternating manner.

6. The dental irrigation system according to claim 1, wherein the laser pulse duration ($t_p$) is in the range of ≥1 µs and <250 µs, and preferably of ≥1 µs and <120 µs.

7. The dental irrigation system according to claim 1, wherein the pulse set (21) consists of two to eight individual pulses (p), and preferably of three to six individual pulses (p).

8. The dental irrigation system according to claim 1, wherein one pulse set (21) has a temporal pulse set length ($t_S$), and wherein the temporal set length ($t_S$) is >1000 µs.

9. The dental irrigation system according to claim 1, wherein a wavelength of the laser beam (5) is chosen such that the laser beam (5) is highly absorbed in the liquid (3).

10. The dental irrigation system according to claim 9, wherein a laser source (4) is one of an Er:YAG laser source having a wavelength of 2940 nm, an Er:YSGG laser source having a wavelength of 2790 nm, an Er,Cr:YSGG laser source having a wavelength of 2780 nm or 2790 nm, or a $CO_2$ laser source having a wavelength of 9300 to 10600 nm.

11. The dental irrigation system according to claim 10, wherein the laser source is an Er:YAG laser having a wavelength of 2940 nm, wherein the laser pulse energy is in a range from 1.0 mJ to 40.0 mJ, and preferably within a range from 5.0 mJ to 20.0 mJ.

12. The dental irrigation system according to claim 9, wherein the handpiece (7) and its exit component (8) are adjusted for both a contact or a non-contact delivery of laser energy to the liquid (3) within the open dental cavity (2), and wherein the exit component (8) has a flat output surface (11) providing a generally parallel exiting beam portion (12) of the laser beam (5).

13. The dental irrigation system according to claim 9, wherein the handpiece (7) and its exit component (8) are adjusted for a contact delivery of laser energy to the liquid (3) within the open dental cavity (2), and wherein the exit component (8) has a substantially conically shaped output surface (13) providing a generally circumferentially spread exiting beam portion (12) of the laser beam (5).

14. The dental irrigation system according to claim 13, wherein the delivery system (6) comprises an articulated arm (14) through which the laser beam (5) is delivered from the laser source (4) to the conically shaped output surface (13).

15. The dental irrigation system according to claim 9, wherein the delivery system (6) further comprises a scanner (15) for scanning one of a flat shaped output surface (11) and a conically shaped output surface (13) of the exit component (8) with the incoming laser beam (5).

16. The dental irrigation system according to claim 9, wherein the handpiece (7) and its exit component (8) are adjusted for a non-contact delivery of laser energy to the liquid (3) within the open dental cavity (2), and wherein optical focusing means (16) are provided to focus the exiting beam portion (12) of the laser beam (5) within the volume of the liquid (3).

17. The dental irrigation system according to claim 1, wherein a wavelength of the laser beam (5) is chosen such that the laser beam (5) is weakly absorbed in the liquid (3), wherein the laser pulse duration is in the range of ≥1 ns and <85 ns, and preferably of ≥1 ns and <25 ns.

18. The dental irrigation system according to claim 17, wherein the laser source (4) is one of a Q-switched Nd:YAG laser source having a wavelength of 1064 nm, a Q-switched ruby laser source having a wavelength of 690 nm, or an alexandrite laser source having a wavelength of 755 nm, including laser sources (4) with frequency doubled wavelengths of these laser sources.

19. The dental irrigation system according to claim 1, wherein the energy of laser pulses (p) within a pulse set is adjustable to gradually decrease linearly or exponentially from the first to the $N^{th}$ pulse (p) within each pulse set, where N is ≥3 and ≤8, however not larger than the total number of pulses (p) within each pulse set.

20. A method for irrigation, including debriding, cleaning and decontamination, of open dental cavities (2) filled with a liquid (3), comprising of the following steps:
providing a laser system (1) comprising a laser source (4) for generating a laser beam (5), an optical delivery system (6) and a treatment handpiece (7) including an exit component (8), wherein the treatment handpiece (7) and its exit component (8) are configured to irradiate the liquid (3) within the open tooth cavity (2) with the laser beam (5) in a contact or non-contact manner, wherein a wavelength of the laser beam (5) is in a range from above 0.4 μm to 11.0 μm inclusive, wherein the laser system is adapted to be operated in pulsed operation with pulse sets (21) containing at least two and maximally twenty individual pulses (p) of a temporally limited pulse length ($t_p$), wherein the pulse sets (21) follow one another with a temporal separation ($T_s$), and wherein the individual pulses (p) follow one another with a pulse repetition rate ($f_p$),
applying said pulsed laser beam (5) to the liquid (3) disposed within the open dental cavity (2) thereby forming at least one vapor bubble (18) in the liquid (3), wherein one single pulse (p) causes the at least one vapor bubble (18) to oscillate between a maximal and a minimal volume with a bubble oscillation frequency ($f_b$);
adjusting the pulse repetition rate ($f_p$) of the individual pulses (p) within one pulse set (21) of the laser beam (5) relative to the bubble oscillation frequency ($f_b$) such, that a synchronization between the delivery of the pulses (p) and the bubble oscillation is achieved,
performing the treatment until desired irrigation, including debriding, cleaning and decontamination, is achieved, or until the temperature rise within the anatomical cavity reaches 3.5 degrees Celsius, whichever occurs first.

21. The method according to claim 20, wherein the pulses (p) are delivered at a pulse repetition rate ($f_p$) in a range from about 1 kHz to about 20 kHz.

22. The method according to claim 20, wherein the pulse sets (21) are delivered with a temporal separation ($T_s$) between the pulse sets (21) of ≥20 ms.

23. The method according to claim 20, further comprising the steps of adjusting the pulse repetition rate ($f_p$) to be at least approximately equal to the bubble oscillation frequency ($f_b$), and delivering the pulses (p) synchronized to the presence of a bubble oscillation intensity minimum.

24. The method according to claim 20, further comprising the steps of adjusting the pulse repetition rate ($f_p$) to be at least approximately equal to the double of the bubble oscillation frequency ($f_b$), and delivering the pulses (p) synchronized to the presence of a bubble oscillation intensity minimum and a bubble oscillation intensity maximum in an alternating manner.

25. The method according to claim 20, wherein a wavelength of the laser beam (5) is chosen such that the laser beam (5) is highly absorbed in the liquid (3), wherein the laser pulse duration is in the range of ≥1 μs and <250 μs, and preferably of ≥1 μs and <120 μs.

26. The method according to claim 25, wherein the liquid (3) is OH-containing, and wherein as a laser source (4) one of an Er:YAG laser having a wavelength of 2940 nm, an Er:YSGG laser having a wavelength of 2790 nm, an Er,Cr:YSGG laser having a wavelength of 2780 nm or 2790 nm, or a $CO_2$ laser having a wavelength of 9300 to 10600 nm is used, and wherein the energy of an individual laser pulse (p) is in a range from 1 mJ to 100 mJ.

27. The method according to claim 26, wherein the laser source is an Er:YAG laser having a wavelength of 2940 nm, wherein the laser pulse energy is in a range from 1.0 mJ to 40.0 mJ, and preferably within a range from 5.0 mJ to 20.0 mJ.

28. The method according to claim 25, wherein the exit component (8) of the handpiece (7) has a flat output surface (11) and provides a generally parallel exiting beam portion (12) of the laser beam (5), wherein the flat output surface (11) is disposed in a distance to the liquid (3) within the open dental cavity (2), and wherein by means of the handpiece (7) and its exit component (8) the laser energy is delivered to the liquid (3) within the open dental cavity (2) in a non-contact manner, thereby generating an elongate vapor bubble (16) in the liquid (3).

29. The method according to claim 25, wherein the exit component (8) of the handpiece (7) has a flat output surface (11) and provides a generally parallel exiting beam portion (12) of the laser beam (5), wherein the flat output surface (11) is immersed in the liquid (3) within the open dental cavity (2), and wherein by means of the handpiece (7) and its exit component (8) the laser energy is delivered to the liquid (3) within the open dental cavity (2) in a contact manner, thereby generating either one of an elongate vapor bubble (16) or a spherical vapor bubble (17) in the liquid (3).

30. The method according to claim 25, wherein the exit component (8) of the handpiece (7) has a substantially conically shaped output surface (13) and provides a generally circumferentially spread exiting beam portion (12) of the laser beam (5), wherein the conically shaped output surface (13) is immersed in the liquid (3) within the open dental cavity (2), and wherein by means of the handpiece (7) and its exit component (8) the laser energy is delivered to the liquid (3) within the open dental cavity (2) in a contact manner, thereby generating a generally spherical vapor bubble (17) in the liquid (3).

31. The method according to claim 30,
wherein the delivery system (6) comprises an articulated arm (14), and wherein the laser beam (5) is delivered from the laser source (4) to the conically shaped output surface (13) through the articulated arm (14).

32. The method according to claim 20,
wherein a wavelength of the laser beam (5) is chosen such that the laser beam (5) is weakly absorbed in the liquid (3), wherein the laser pulse duration is in the range of ≥1 ns and <85 ns, and preferably of ≥1 ns and <25 ns.

33. The method according to claim 32,
wherein the liquid (3) is OH-containing, and wherein as a laser source (4) one of a Q-switched Nd:YAG laser source having a wavelength of 1064 nm, a Q-switched ruby laser source having a wavelength of 690 nm, or an alexandrite laser source having a wavelength of 755 nm is used, including laser sources (4) with frequency doubled wavelengths of these laser sources.

34. The method according to claim 32,
wherein optical focusing means (16) are provided, wherein the exit component (8) of the handpiece (7) is disposed in a distance to the liquid (3) within the anatomical cavity (2), and wherein by means of the optical focusing means (16) the laser energy is focused in the liquid (3) within the open dental cavity (2), thereby delivering the laser energy to the liquid (3) in a non-contact manner, and thereby generating a generally spherical vapor bubble (17) in the liquid (3).

35. The method according to claim 32,
wherein the delivery system (6) further comprises a scanner (15), and wherein one of a flat shaped output surface (11) and a conically shaped output surface (13) of the exit component (8) is scanned with the incoming laser beam (5) by means of the scanner (15).

36. The method according to claim 20,
wherein the pulse set (21) consists of two to eight individual pulses (p), and preferably of three to six individual pulses (p).

37. The method according to claim 20,
wherein one pulse set (21) has a temporal pulse set length ($t_S$), and wherein the temporal set length ($t_S$) is >1000 µs.

38. The method according to claim 20,
wherein the energy of laser pulses (p) within a pulse set is adjusted by one of the user or a control system of the laser system (1) to gradually decrease linearly or exponentially from the first to the $N^{th}$ pulse within each pulse set, where N is ≥3 and ≤8, however not larger than the total number of pulses (p) within each set.

39. A method for irrigation, including debriding, cleaning and decontamination, of open dental cavities (2) filled with liquid (3), comprising of the following steps:
providing a laser system (1) comprising a laser source (4) for generating a laser beam (5), an optical delivery system (6) and a treatment handpiece (7) including an exit component (8), wherein the optical delivery system (6) comprises an articulated arm (14), wherein the handpiece (7) and its exit component (8) are configured to irradiate the liquid (3) within the open tooth cavity (2) in a contact manner, wherein the exit component (8) has a conical output surface (13), wherein a wavelength of the laser beam (5) is in a range from above 0.4 µm, inclusive, to 11.0 µm inclusive, wherein the laser system (1) is adapted to be operated in pulsed operation with pulse sets (21) containing at least one and maximally twenty individual pulses (p) of a temporally limited pulse length ($t_p$), wherein the laser pulse length ($t_p$) is in the range of ≥1 µs and <250 µs, wherein the pulse repetition rate is in the range from 1 kHz, including, to 20 kHz, including, and wherein a temporal separation ($T_S$) between the pulse sets (21) is ≥20 ms;
applying said pulsed laser light in a contact manner to the liquid (3) disposed in the open dental cavity (2) thereby forming a vapor bubble (18); and
performing the treatment until desired irrigation, including debriding, cleaning and decontamination, is achieved, or until the temperature rise within the anatomical cavity reaches 3.5 degrees Celsius, whichever occurs first.

40. The method of claim 39,
wherein the laser pulse length ($t_p$) is in the range of ≥1 µs and <120 µs.

41. The method of claim 39,
wherein the laser system (1) is configured to generate coherent light having a wavelength highly absorbed in OH-containing liquids, by means of one of an Er:YAG laser source having a wavelength of 2940 nm, an Er:YSGG laser source having a wavelength of 2790 nm, an Er,Cr:YSGG laser source having a wavelength of 2780 nm or 2790 nm, and a $CO_2$ laser source having a wavelength of 9300 to 10600 nm, and wherein laser pulse energy is in a range from 1 mJ to 100 mJ.

42. The method of claim 39,
wherein the laser source (4) is an Er:YAG laser source having a wavelength of 2940 nm, wherein laser pulse energy is in a range from 1 mJ to 40 mJ, wherein the exit component (8) is cylindrical, having a diameter (D) between 200 µm and 1000 µm, wherein the conical output surface (13) has a conical half angle α being in the range from 16° to 38°, wherein the temporal separation ($T_S$) between pulse sets (21) is <0.5 s, and wherein the cumulative delivered energy during a treatment is below 150 J.

43. The method of claim 42,
wherein the conical half angle α is in the range from 34° to 38°.

44. A method for irrigation, including debriding, cleaning and decontamination, of open dental cavities (2) filled with liquid (3), comprising of the following steps:
providing a laser system (1) comprising a laser source (4) for generating a laser beam (5), an optical delivery system (6) and a treatment handpiece (7) including an exit component (8), wherein the handpiece (7) and its exit component (8) are configured to irradiate the liquid (3) within the open tooth cavity (2) in a contact manner, wherein the exit component (8) has a flat or conical output surface (13), wherein a wavelength of the laser beam (5) is in a range from above 0.4 µm, inclusive, to 11.0 µm inclusive, wherein the laser system (1) is adapted to be operated in pulsed operation with pulse sets (21) containing at least two and maximally four individual pulses (p) of a temporally limited pulse length ($t_p$), wherein the laser pulse length ($t_p$) is in the range of ≥1 µs and <120 µs, wherein a temporal separation ($T_S$) between the pulse sets (21) is ≥20 ms, and wherein the individual pulses (p) follow one another with a pulse repetition rate ($f_p$) within a range of 1 kHz, inclusive, to 20 kHz, inclusive; and applying said pulsed laser light in a contact manner to the liquid (3) disposed in the anatomical cavity (2) thereby forming a vapor bubble (18); and performing the treatment until desired irrigation, including debriding, cleaning and decontamination, is achieved, or until the temperature rise within the anatomical cavity reaches 3.5 degrees Celsius, whichever occurs first.

45. The method of claim 44, wherein the laser system (1) is configured to generate coherent light having a wavelength highly absorbed in OH-containing liquids, by means of one of an Er:YAG laser source having a wavelength of 2940 nm, an Er:YSGG laser source having a wavelength of 2790 nm, an Er,Cr:YSGG laser source having a wavelength of 2780 nm or 2790 nm, and a $CO_2$ laser source having a wavelength of 9300 to 10600 nm, and wherein laser pulse energy is in a range from 1 mJ to 100 mJ.

46. The method of claim 44, wherein the laser source (4) is an Er:YAG laser source having a wavelength of 2940 nm, wherein laser pulse energy is in a range from 1 mJ to 40 mJ, wherein the exit component (8) is cylindrical, having a diameter (D) between 200 μm and 1000 μm, and wherein the conical output surface (13) has a conical half angle α being in the range from 16° to 38°.

47. The method according to claim 44, wherein the delivery system (6) comprises an articulated arm (14) through which the laser beam (5) is delivered from the laser source (4) to the conically shaped output surface (13).

* * * * *